(12) United States Patent
Ando et al.

(10) Patent No.: US 7,881,533 B2
(45) Date of Patent: Feb. 1, 2011

(54) MICROINJECTION APPARATUS AND MICROINJECTION METHOD

(75) Inventors: Moritoshi Ando, Kawasaki (JP); Sachihiro Youoku, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 1108 days.

(21) Appl. No.: 11/601,626

(22) Filed: Nov. 20, 2006

(65) Prior Publication Data

US 2008/0126051 A1  May 29, 2008

(30) Foreign Application Priority Data

Jul. 28, 2006  (JP) ............................. 2006-206963

(51) Int. Cl.
*G06K 9/34* (2006.01)
(52) U.S. Cl. ..................... 382/181; 348/159; 435/285.1
(58) Field of Classification Search ................... 703/11; 435/286.2; 348/159; 382/181, 199
See application file for complete search history.

(56) References Cited

U.S. PATENT DOCUMENTS

| | | | |
|---|---|---|---|
| 2,472,907 A * | 6/1949 | Kolesnikoff | 355/62 |
| 6,593,129 B1 * | 7/2003 | Takeshita et al. | 435/285.1 |
| 6,845,177 B2 * | 1/2005 | Chiu | 382/199 |
| 7,479,388 B2 * | 1/2009 | Ando | 435/285.1 |
| 2005/0244948 A1 * | 11/2005 | Ando | 435/285.1 |
| 2006/0024812 A1 * | 2/2006 | Youoku et al. | 435/285.1 |
| 2007/0149984 A1 * | 6/2007 | Nishiyama et al. | 606/116 |

FOREIGN PATENT DOCUMENTS

JP  2624719  4/1997

* cited by examiner

*Primary Examiner*—Daniel G Mariam
*Assistant Examiner*—Aklilu k Woldemariam
(74) *Attorney, Agent, or Firm*—Fujitsu Patent Center

(57) ABSTRACT

A microinjection apparatus of the present invention includes a needle-position polarity detecting unit that detects a position of the needle in the vertical direction at which a value of a differential aggregate distribution becomes the maximum in the situation in which a shape of the leading edge of the needle at a focal position narrows at the right. Moreover, a differential-average determining unit, based on a differential average of an image near the position detected by the needle-position polarity detecting unit, determines the lowest allowable position of the needle, which is a position at which a differential average exceeds a predetermined threshold.

13 Claims, 27 Drawing Sheets

DEFOCUSED IMAGE

DEFOCUSED/BINARIZED

DEFOCUSED/BINARIZED

DIAGRAM OF PROCESSED IMAGE OF CELL IN
NEEDLE POSITION

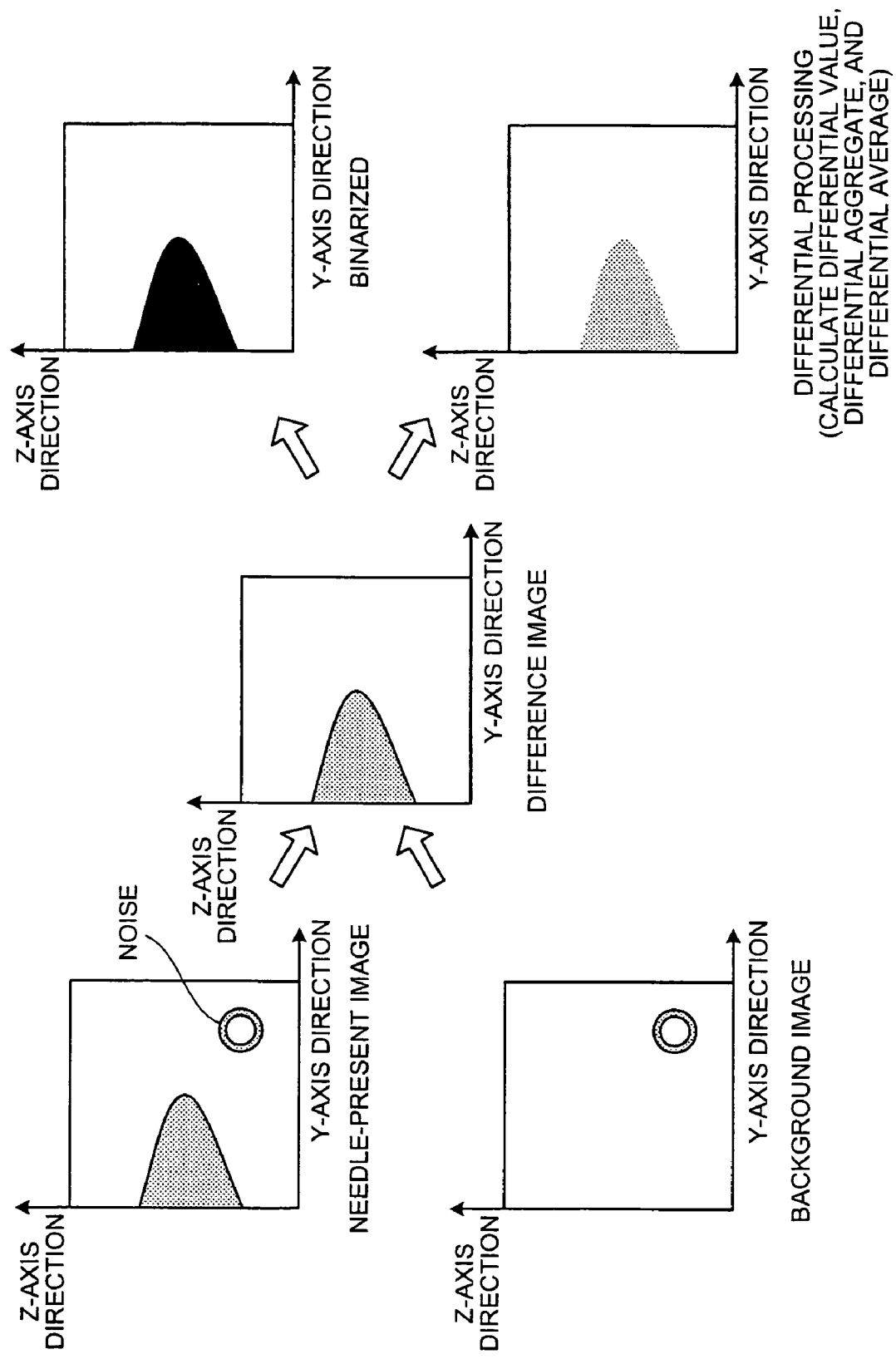

BACKGROUND IMAGE

NEEDLE IMAGE

DIFFERENCE IMAGE

DIFFERENTIAL IMAGE

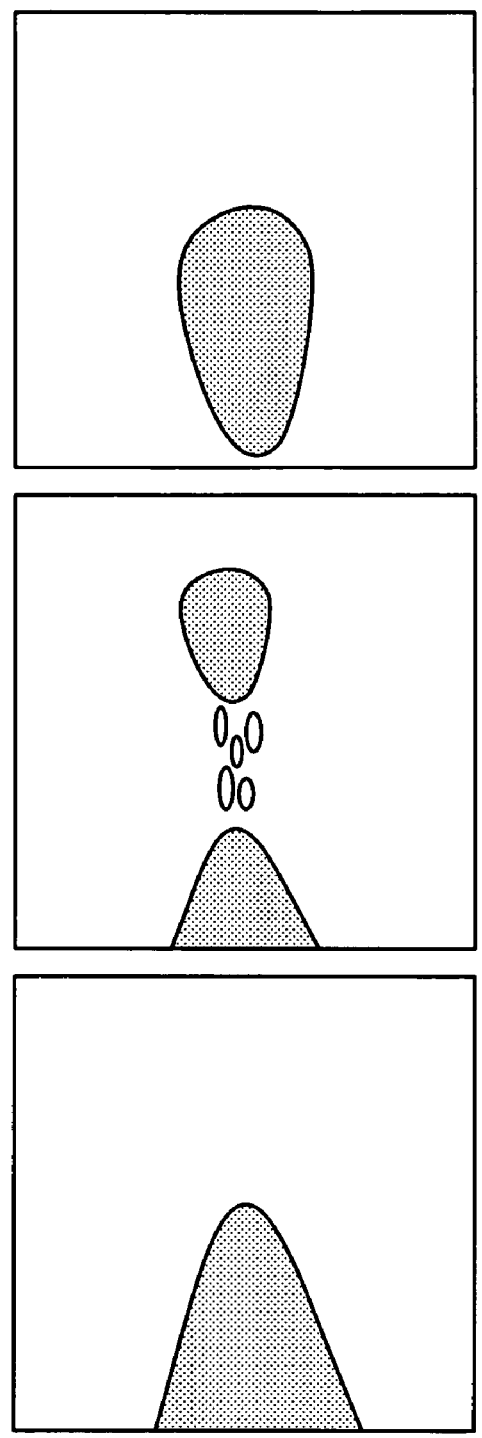

UPPER BLUR REGION
(FOCAL PLANE +100 μm)

FOCUSED (FOCAL PLANE)

SLIGHTLY LOW
(FOCAL PLANE -20 μm)

LOWER BLUR REGION
(FOCAL PLANE -100 μm)

MICROINJECTION APPARATUS AND MICROINJECTION METHOD

CROSS REFERENCE TO RELATED APPLICATIONS

This application claims the benefit under 35 U.S.C. Section 119 of Japanese Patent Application No. 2006-206963, filed Jul. 28, 2006, which is hereby incorporated by reference in its entirety into this application.

BACKGROUND OF THE INVENTION

1. Field of the Invention

The present invention generally relates to a technology for injecting an object into the cell with a needle. The present invention specifically relates to determining an operation start position of the needle.

2. Description of the Related Art

A study of an alteration of genetic information of a cell by running a microscopic needle into the cell and injecting a gene (microinjection), using a microscope clarifies a role of the gene and permits a tailor-made medicine of conducting gene treatment in accordance with individual genetic characteristics. Such study has made it possible to cure illness attributable to genetic causes that have heretofore been incurable.

The methods for injecting a gene into the cell can be, e.g., an electric method (electroporation), a chemical method (lipofection), a biological method (vector method), a mechanical method (microinjection), etc.

Among those methods, the electrical method includes breaking a cell membrane by running a large current, giving a big damage to the cell. The chemical method is limited in the number of genes to be introduced and is poor in respect of introduction efficiency. The biological method has the defects such as that it there is a limitation on the number of materials to be introduced and that safety of this method cannot be confirmed.

As a result, at present, in many cases, the mechanical method is employed as the safest and the most efficient method. For example, Japanese Patent No. 2624719 discloses a technology regarding the microinjection apparatus that arranges cells in regular order and automatically performs the microinjection.

However, in the conventional technology, while an adjustment must be made of the position of the needle for the injection into the cell as an object with accuracy of ±1 μm, this adjustment must be made manually by an experienced worker. Moreover, the length of the needle can have an error of the order of ±2 mm, and to take the error into account, the adjustment of the needle position becomes essential. Therefore, each time a needle is changed, adjustment of the position of the needle must be conducted manually by an experienced worker, forcing an increase in working hour and workload.

Thus, there is a need of a technology that permits easy and efficient adjustment of position of the needle.

SUMMARY OF THE INVENTION

It is an object of the present invention to at least partially solve the problems in the conventional technology.

According to an aspect of the present invention, a microinjection apparatus that injects an object into an adherent cell with a needle, the needle being variable in its position in a first direction, includes an image acquiring unit that acquires a magnified image of a leading edge of the needle; a needle detecting unit that detects the leading edge of the needle in the magnified image; a shape judging unit that determines a shape of the leading edge of the needle in the magnified image when a differential aggregate calculated from the image of the leading edge of the needle detected by the needle detecting unit is lower than a first threshold; and a needle shifting unit that shifts the needle in the first direction according to the shape of the leading edge judged by the shape judging unit.

According to another aspect of the present invention, a method of microinjection of injecting an object into an adherent cell with a needle, the needle being variable in its position in a first direction, includes acquiring a magnified image of a leading edge of the needle with an image acquiring unit; detecting the leading edge of the needle in the magnified image; determining a shape of the leading edge of the needle in the magnified image when a differential aggregate calculated from the image of the leading edge of the needle detected by the needle detecting unit is lower than a first threshold; and shifting the needle in the first direction according to the shape of the leading edge judged by the shape judging unit.

The above and other objects, features advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 9 is a schematic for explaining the image processing in the needle detection processing;

FIG. 11 is a schematic for explaining the difference image judging method;

DETAILED DESCRIPTION OF THE PREFERRED EMBODIMENTS

Exemplary embodiments of the present invention will now be described in detail by referring to the accompanying drawings.

The embodiments relate to automatically illuminating a cell that is located at a bottom surface of a petri dish, and while watching the cell with a CCD camera, adjusting a vertical position of a capillary and injecting an object present in the capillary into the adherent cell.

Figure 1:
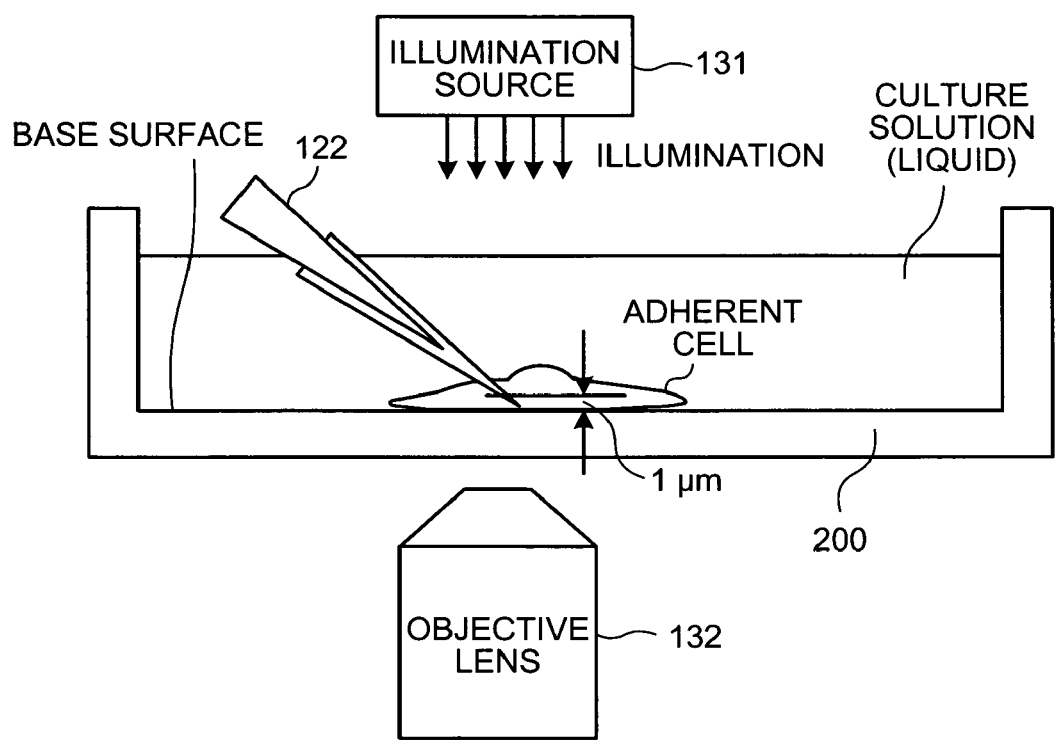
FIG. 1 is a schematic for explaining the technique of microinjection.

FIG. 1 is a schematic for explaining the technique of microinjection into an adherent cell. An adherent cell is a cell that has a nature of adhering to other cells and, by concentration of same kind of cells, constitutes a part of a living organism. Thus, an adherent cell has the nature opposite to that of a non-adherent cell, or a floating cell, such as a red blood cell, which does not have the nature of adherence and functions floating alone.

As shown in FIG. 1, when performing microinjection into an adherent cell, the adherent cell is placed on the bottom surface of the petri dish 200 that is filled with fluid such as a culture solution. An illumination source 131 illuminates an area surrounding the adherent cell and an objective lens 132 arranged under the petri dish 200 obtains a magnified image of the adherent cell. In this state, a needle 122 is guided into the adherent cell making use of the magnified image of the adherent cell and an object present in the needle 122 is injected into the adherent cell. The object can be a gene.

A plate having minute holes can be provided on the bottom surface of the petri dish, and cells are captured in those minute holes, but in the following description, the case of not using the plate has been explained. Moreover, the bottom surface of the petri dish is referred to as a base surface.

The adherent cell is substantially flat on the bottom surface of the petri dish 200. In other words, while the cell has an area of 20 μm to 30 μm in the horizontal direction, it has a thickness of only 5 μm or so in the vertical direction. To puncture the adherent cell with the leading edge of the needle 122 and efficiently inject a gene into the adherent cell, the needle 122 is lowered at a high speed to a distance of around 1 μm above the base surface. To operate the needle 122 in this manner, i.e., without touching the base surface, requires high experience and skill.

The reason for such difficulty of the control of the needle 122 is that a border between the cell and the petri dish is not clear due to the transparency of the adherent cell and a transparent material making up the petri dish that has the adherent cell adhere to the bottom surface thereof and that a perspective and three-dimensional feeling is hard to grasp because observation is made basically using one objective lens only.

The needle 122 can be freely moved in horizontal direction and in vertical direction and therefore, even if a visual field of the objective lens is fixed to a certain point of observation position, it is possible that the needle 122 is not present within this visual field. It is also possible that it takes considerable times of trial and error and sometimes becomes very burdensome to move a needle control stage that controls the position of the needle 122 and make manual adjustments so that the leading edge of the needle 122 comes within the visual field of the objective lens and at the same time, the leading edge gets in touch with the adherent cell. The present invention was made to solve these problems.

Figure 2:
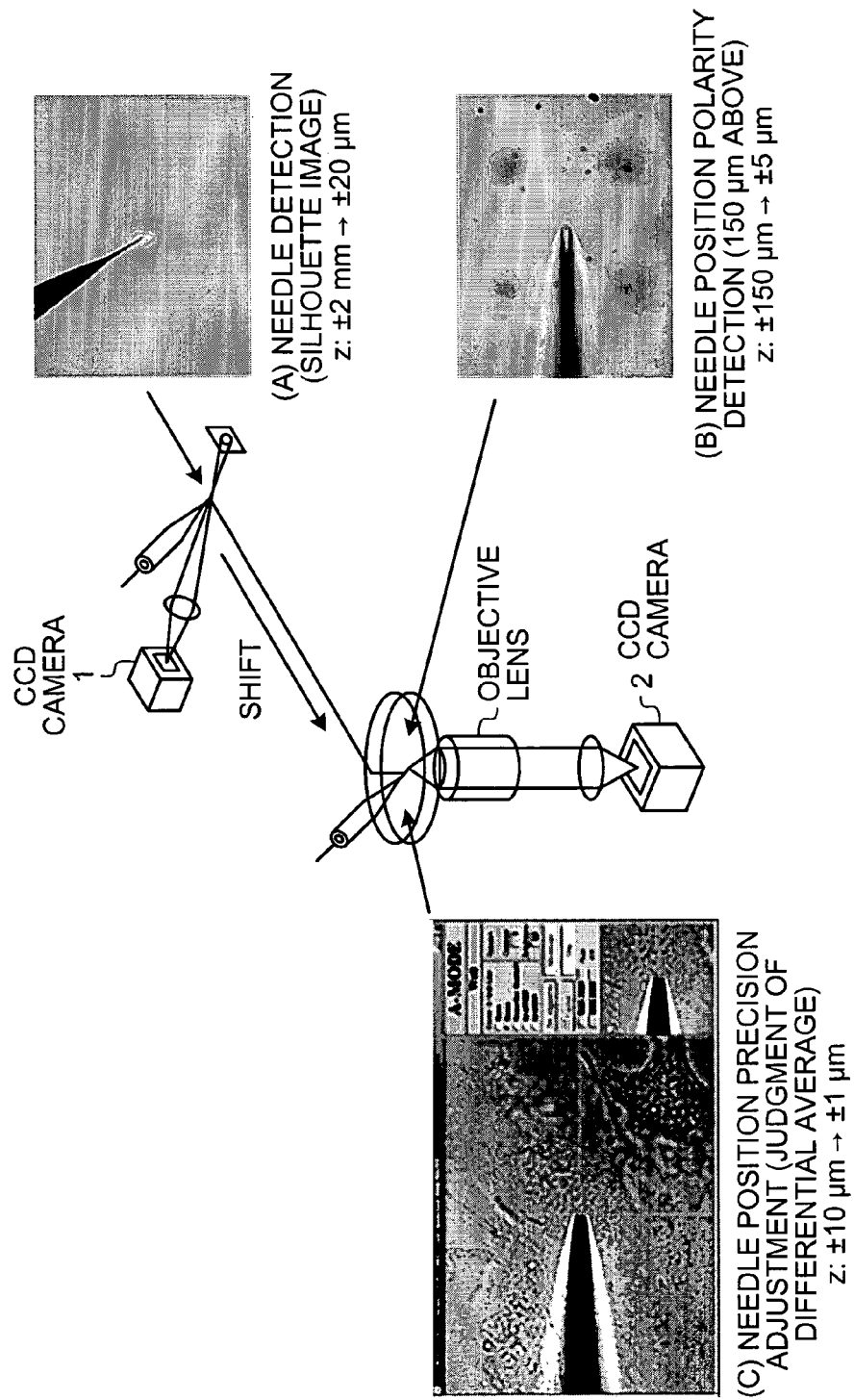
FIG. 2 is a schematic for explaining a needle position automatic adjustment method according to an embodiment of the present invention.

A microinjection apparatus and a microinjection method according to an embodiment of the present invention will now be described with reference to FIGS. 2 to 23. Schematic description will firstly be made of the processing of a needle position automatic adjustment method according to the embodiment, referring to FIG. 2. FIG. 2 is an explanatory diagram for a schematic description of the processing of the needle position automatic adjustment method according to the embodiment.

Firstly, as shown in (A) in FIG. 2, a needle detection processing is performed. In this processing, a silhouette image of the leading edge of only the needle is taken using a CCD camera 1. That is, the silhouette image of the leading edge of the needle is taken when no cell is present within a visual field of an objective lens. By detecting the needle from within the taken image and moving the leading edge of the needle to the center of the visual field, a position of the needle in horizontal direction is fixed. Through this processing, a rough position of the needle in vertical direction is obtained. An error of this position is narrowed to ±20 μm from ±2 mm which is the error of position before the processing.

Next, as shown in (B) in FIG. 2, a needle position polarity detection processing is performed. In this processing, the needle detected in needle detection processing (A) is lowered in the horizontal direction by about 150 μm thereby bringing the leading edge of the needle is still closer to the adherent cell, and a differential aggregate and a polarity (direction of needle) of an image of the needle newly taken at this position is judged. Through this process, rough position of the needle in the vertical direction is obtained. The error in the position is narrowed to ±5 μm from ±150 μm that is the error of the position before the processing.

Next, as shown in (C) in FIG. 2, a needle position precision adjustment processing is performed. In this processing, while shifting the position of the needle step by step either upward or downward in the vertical direction, starting from the rough position of the needle in vertical direction obtained in (B), a differential average of the scanned image of the leading edge of the needle is judged, determining that the position of the needle at which this differential average is closest to a predetermined threshold is the position at which the needle gets in touch with the adherent cell. The error of the position at which the needle gets in touch with the adherent cell is narrowed to ±1 μm from ±10 μm that is the error of the position before the processing.

To make the description easier, FIG. 2 shows a CCD camera 1 that takes an image of the needle in the needle detection processing, i.e., (A) in FIG. 2, and a CCD camera 2 that takes an image of the needle in the needle position precision adjustment processing, i.e., (C) in FIG. 2, as two different cameras, but in fact, there is only one camera with variable position. Of course, separate cameras can be employed.

Figure 3:
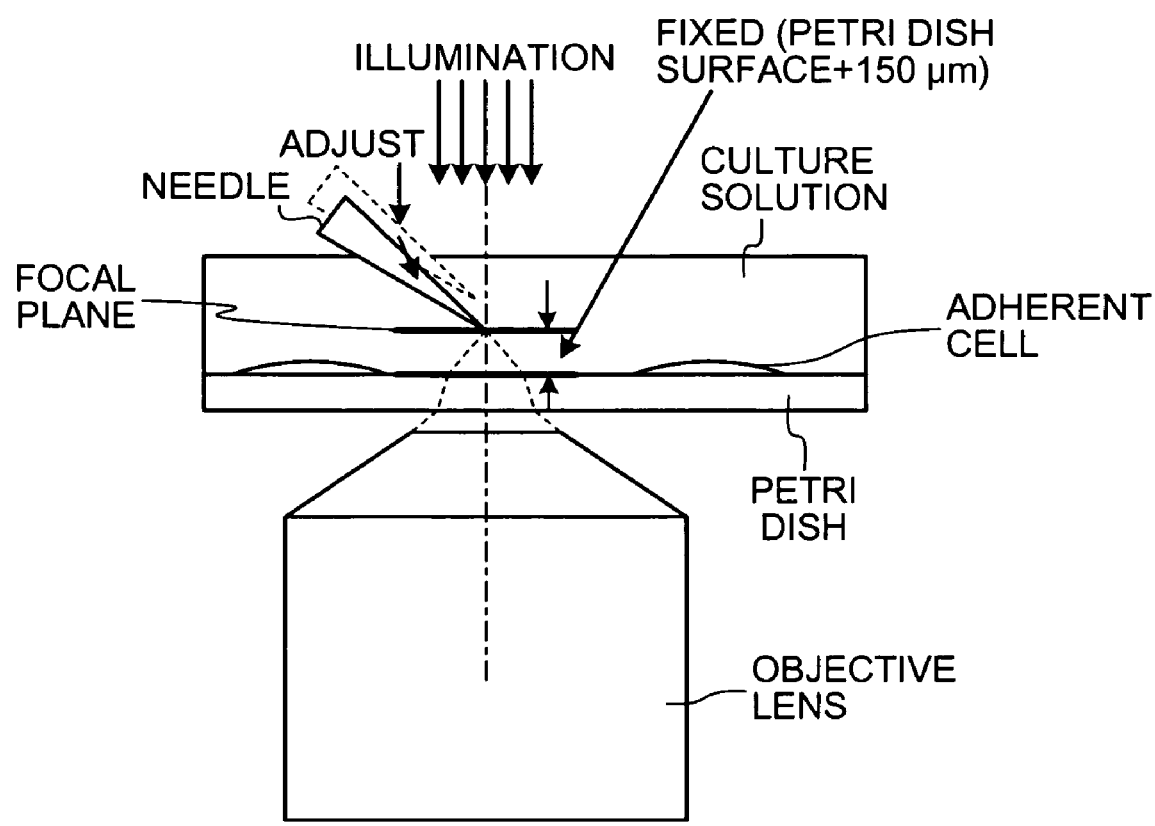
FIG. 3 is a side view of an optical system according to the embodiment.

FIG. 3 is a schematic for explaining the optical system according to the embodiment. As shown in FIG. 3, a light is irradiated by illumination from above the petri dish having the culture solution within and the adherent cell adhering to its base surface, and the adherent cell on the petri dish is observed through the objective lens from below the petri dish. The needle is arranged in such a manner that the leading edge thereof is directed, inclined, toward below the petri dish. The needle can have its position adjusted up and down in vertical direction.

As shown in FIG. 3, a focal plane of the objective lens is positioned 150 μm above the base surface of the petri dish. In this condition, the processing of automatically bringing the leading edge of the needle close to the focal plane without touching the base surface is an object of the embodiment. By automatically performing the processing of bringing the leading edge of the needle close to the focal plane without touching the base surface, even an inexperienced man can easily bring the leading edge of the needle in touch with the focal plane without damaging the needle. This also permits a reduced workload of the microinjection and a heightened work efficiency thereof.

Figure 4:
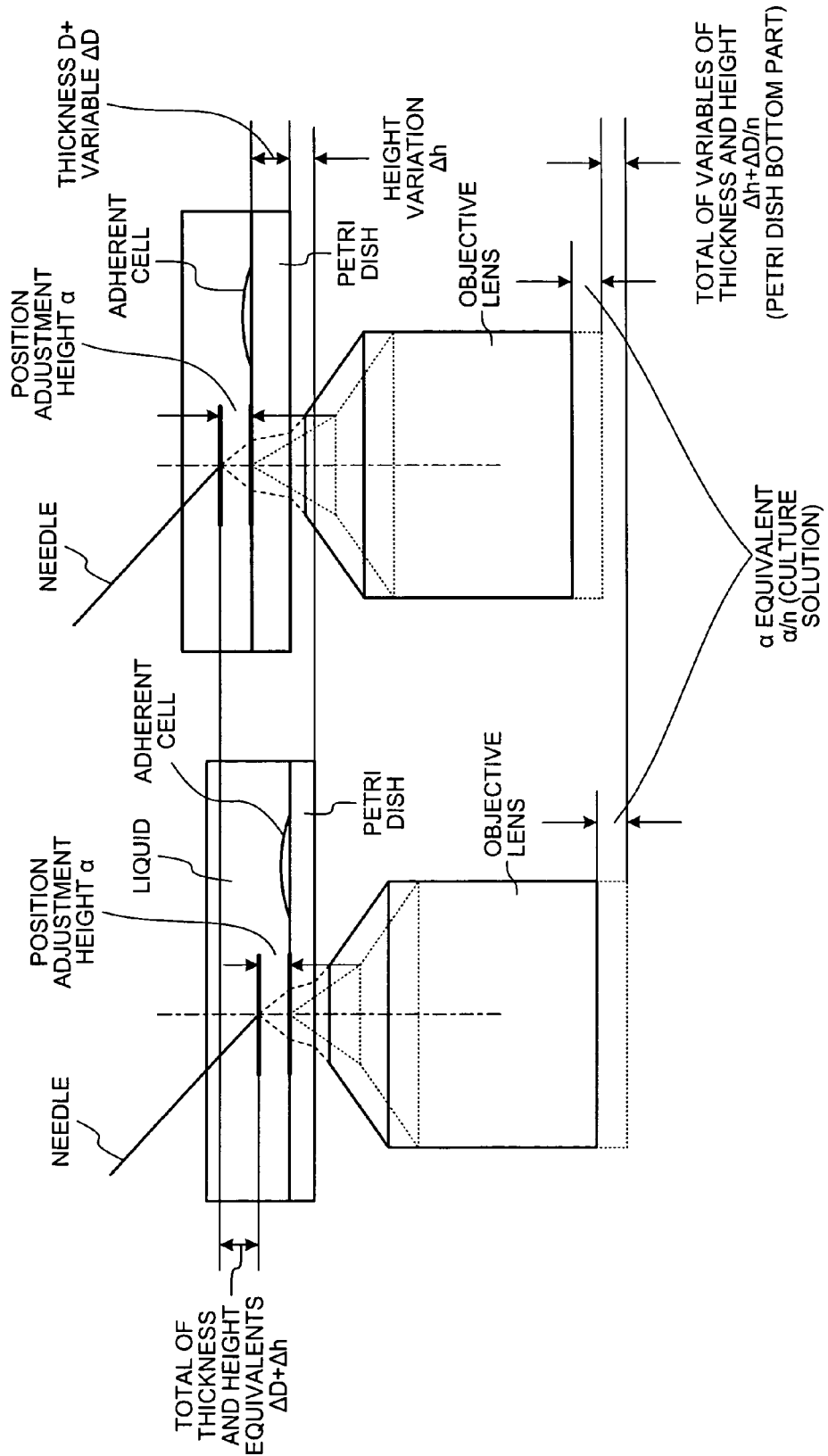
FIG. 4 is a schematic for explaining the factors that affect needle position.

Factors affecting the needle position adjustment of the embodiment will now be described. FIG. 4 is an explanatory diagram for a description of factors affecting the needle position adjustment of the embodiment. In the optical system of the embodiment, a control position (x,y,z1) of the needle and a focal point control position (z2) of the objective lens must be in alignment with each other. Here, x and y of the control position (x,y,z1) of the needle represent a two-dimensional coordinate at a horizontal plane of the needle control stage, and z1 represents a depth of the needle in the direction in which the needle is fixed to the needle control stage. The depth is a parameter indicative of the position of the needle in vertical direction. The focal point control position Z2 of the objective lens represents a focal position of the objective lens indicative of a height position of the objective lens. A height adjustment of the needle using the objective lens can be made only after Z1 and Z2 correspond with each other.

As shown in FIG. 4, by firstly causing the objective lens to focus on the surface of the cell, then shifting the objective lens by a volume equivalent to a position adjustment height α and shifting the needle by a volume corresponding to the shift α of the objective lens, the coordinates of the depth z1 of the needle and of the focal point control position z2 of the objective lens can be made to correspond with each other.

To measure the upward shift equivalent to α, if an object is within a material of refractive index n, moving the objective lens by Δz is enough. Δz is expressed by Equation (1):

$$\Delta z = \alpha / n \quad (1)$$

Incidentally, even if petri dishes are of the same kind, a bottom position and a thickness are different from one petri dish to another. As a result, when a lower part of a standard petri dish as a basis is taken as an original point, two changing factors arise; a position variable Δh of a bottom position of a working petri dish used for the microinjection work and a thickness variable ΔD of the working petri dish. The position variable Δh of the bottom position of the working petri dish is a variation of a separation distance in a situation where the bottom of the working petri dish is further separated from an arrangement plane as it comes nearer to the center of the petri dish. Namely, generally, the petri dish, only at the outer circumference of the bottom face, is in touch with the arrangement plane on which the petri dish is arranged. In this condition, a needle position variable $\Delta Z_{cap}$ from the standard position of the standard petri dish is expressed by Equation (2):

$$\Delta z_{cap} = \Delta h + \Delta D \quad (2)$$

However, when a height of the working petri dish is measured by a focal point automatic adjustment method using the adherent cell, a shift distance ΔZ of the objective lens is expressed by Equation (3) where $n_1$ is a refractive index of the material of the working petri dish. The focal point automatic adjustment method using the adherent cell is a method of automatically detecting the adherent cell and adjusting the focal point in the microinjection by detecting a maximum focal position of the objective lens at which a maximum value is shown by the differential aggregate distribution based on the image of the adherent cell taken at each focal position of a first focal interval, at an observation position of the petri dish at which presence or absence of the adherent cell is judged and presence of the adherent cell is detected and by detecting a minimum focal position of the objective lens at which a minimum value is shown by the differential aggregate distribution based on the image of the adherent cell taken at each focal position of a second focal interval, narrower than the first interval, within a predetermined range including the maximum focal position at this observation position.

$$\Delta Z = \Delta h + \Delta D / n_1 \quad (3)$$

Equation (3) is transformed as follows:

$$\Delta h = \Delta Z - \Delta D / n_1 \quad (4)$$

If Δh is substituted into Equation (2), $\Delta Z_{cap}$ can be expressed as shown by Equation (5):

$$\Delta z_{cap} = \Delta Z - \Delta D (1/n_1 + 1) \quad (5)$$

Equation (6) applies:

$$\Delta D = n_1 (\Delta Z - \Delta n) \quad (6)$$

Hence, $\Delta Z_{cap}$ is further expressed as shown by Equation (7):

$$\Delta z cap = \Delta h + n1(\Delta Z - \Delta h) = n1 \Delta Z + \Delta h(1 - n1) \quad (7)$$

Since ΔD can not directly be measured, $\Delta Z_{cap}$ can not be obtained expressly. However, by putting $n_1 = 1.5$ into Equation (5), $\Delta Z_{cap}$ can be expressed as shown by Equation (8):

$$\Delta z cap = \Delta Z - \frac{5}{3} \Delta D \quad (8)$$

On the other hand, by putting $n_1 = 1.5$ into Equation (7), $\Delta Z_{cap}$ can be expressed as shown by Equation (9):

$$\Delta z cap = 1.5 \Delta Z - 0.5 \Delta h \quad (9)$$

If the position variable Δh of the bottom position of the working petri dish can be deemed to be smaller than the thickness variable ΔD of the working petri dish, then the following expression applies:

$$\Delta h < \Delta D \quad (10)$$

This shows that if the Δh term is neglected as an error, $\Delta Z_{cap}$ can be expressed only by the ΔZ term with only an error of half of Δh at best. Namely, $\Delta Z_{cap}$ can be expressed with a single term of ΔZ as shown by Equation (11). In this manner, an approximate value of $\Delta Z_{cap}$ is calculated.

$$\Delta z cap = 1.5 \Delta Z \quad (11)$$

Namely, by clarifying a positional relationship of the needle and the microscope height of a control system, using the standard petri dish, by obtaining the height of the working petri dish by the focal point automatic adjustment method using the adherent cell, by expressing a difference between the position of the objective lens of the microscope and the standard value as ΔZ, and by offsetting the needle position by 1.5ΔZ relative to the standard position, the positional adjustment can be made of the needle position in vertical direction (direction of height) considering the effect of thickness variation of the petri dish.

Figure 22:
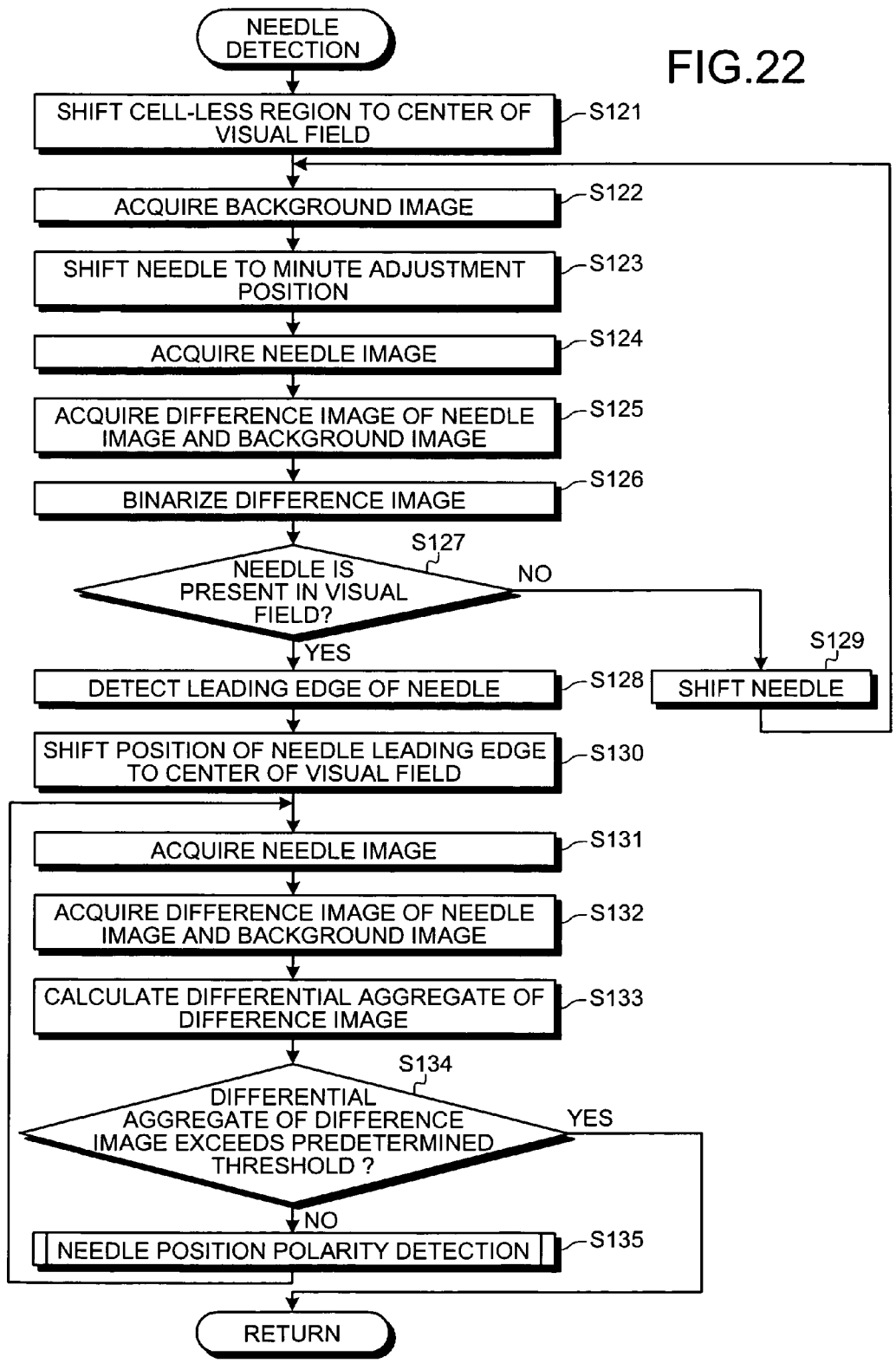
FIG. 22 is a flowchart of the needle detection processing procedure.

When a position adjustment of the height of the needle (vertical direction) is made using such method, for example, in the step S123 shown in FIG. 22, the position of the height of the needle (vertical direction) can be shifted to an appropriate position prior to all processing of the needle position automatic adjustment as an object of the present embodiment, and the processing efficiency is heightened of the needle position automatic adjustment and the adjustment can be performed speedily. With respect to the needle search start position, the variable (Δh) from a first standard value (height of the petri dish as a standard) of the vertical position of the petri dish and the variable (ΔD) from a second standard value (thickness of the petri dish as a standard) of the thickness of bottom part of the petri dish must be taken into consideration. When the variable (Δh) from the first standard value is small as compared with the variable (ΔD) from the second standard value, the position of the needle in vertical direction can be determined by adding the variable of the thickness of the bottom part multiplied by the refractive index of the bottom part, and therefore, in vertical direction, the needle position search can be performed with a low workload and speedily.

Figure 5:
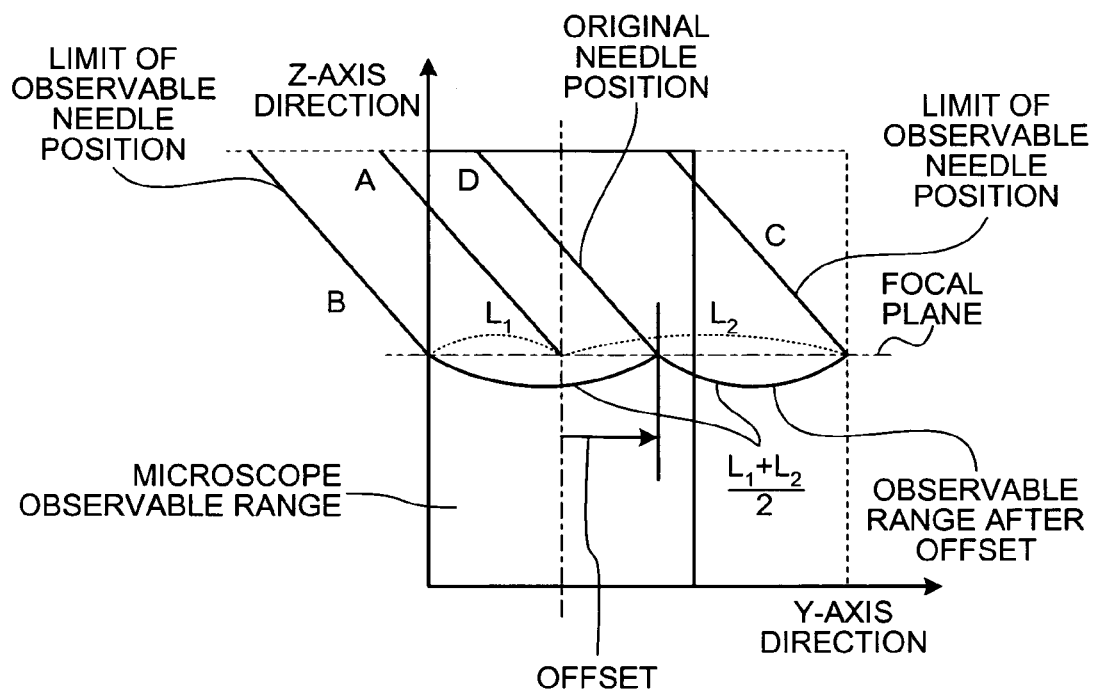
FIG. 5 is a graph for explaining the offset of the needle position.

The offset of the needle position of the embodiment will now be described. FIG. 5 is a schematic for explaining the offset of the needle position of the embodiment. FIG. 5 is a diagram of a projection of the needle, fixed to the needle control stage at a given acute angle with the horizontal direction in such manner that the leading edge thereof is directed toward the visual field of the objective lens, onto a Y-Z plane where a direction forming a supplementary angle to the given acute angle is expressed as Y-axis direction and the vertical direction is expressed as Z-axis direction.

In this Y-Z plane, a part surrounded by a rectangle shown by a solid line is a range that can be observed by the objective lens of a microscope. This rectangle is referred to as a microscope observable range. A part surrounded by an approximate square shown by a dotted line is an observable range within which any part of the needle can be caught by the objective lens of the microscope. This approximate square is referred to as a needle catchable range. Normally, the needle is at the needle position A and the leading edge thereof is in touch with the focal plane at the center of a petri dish stage. In Y-axis direction, the needle position at which the leading edge of the needle is within the microscope observable range and Y becomes minimum is the needle position B, and this position is the limit of the needle position that can be observed. In X-axis direction, the needle position at which the leading edge of the needle is within the microscope observable range and X becomes maximum is the needle position C, and this position as well is the limit of the needle position that can be observed. Namely, when the needle position is between position B and position C, the leading edge of the needle can be observed by the microscope.

As shown in FIG. 5, in case of shifting the needle from the needle position A to the needle position B, if the shift distance exceeds L1, the leading edge of the needle goes beyond the microscope observable range and therefore, the needle gets out of the needle catchable range. In case of shifting the needle from the needle position A to the needle position C, if the shift distance exceeds L2, a root part of the needle goes beyond the microscope observable range and therefore, the needle gets out of the needle catchable range. Since L1 is smaller than L2, there is a difference in the shift distance within which a stay at the microscope observable range can be maintained, between the case of shifting the needle from the needle position A to the needle position B and the case of shifting the needle from the needle position A to the needle position C. Therefore, especially in the case of shifting the needle from the needle position A to the needle position B, there was a problem that the leading edge of the needle easily gets out of the visual field of the objective lens.

Therefore, in the present embodiment, the offsetting of the needle position is conducted so that the leading edge D of the needle at the focal plane comes to the middle point of the position of the leading edge of the needle at the needle position B and the position of the leading edge of the needle at the needle position C. This middle point is adjusted so that the distance to the position of the leading edge of the needle at the needle position B and the distance to the position of the leading edge of the needle at the needle position C become equally (L1+L2)/2. L1 depends on a magnitude of the domain of the microscope observable range and L2 depends on the magnitude of the domain of the microscope observable range, length of the needle, and a degree of the cute angle with the horizontal direction. Namely, L1 and L2 are dependent on structural attributes of the microinjection apparatus and are uniquely determined parameters.

When an adjustment is made of the position of the needle in horizontal direction, using such method, for example, in the step S123 shown in FIG. 22, the position of the needle in horizontal direction can be shifted to an appropriate position prior to all processing of the needle position automatic adjustment as an object of the present embodiment, and the processing efficiency is heightened of the needle position automatic adjustment and the adjustment can be performed speedily. When the needle position automatic adjustment is started from thus offset-adjusted position, an inefficiency of losing sight of the leading edge of the needle from the visual field of the objective lens can be prevented from occurring. Namely, since the leading edge of the needle is offset by a predetermined amount in the direction forming a supplementary angle to a given acute angle at a horizontal plane and taking of an image including the leading edge of the needle is started with such needle position taken as the work start position, the needle position search can be performed with a low workload and speedily in horizontal direction.

Figure 6:
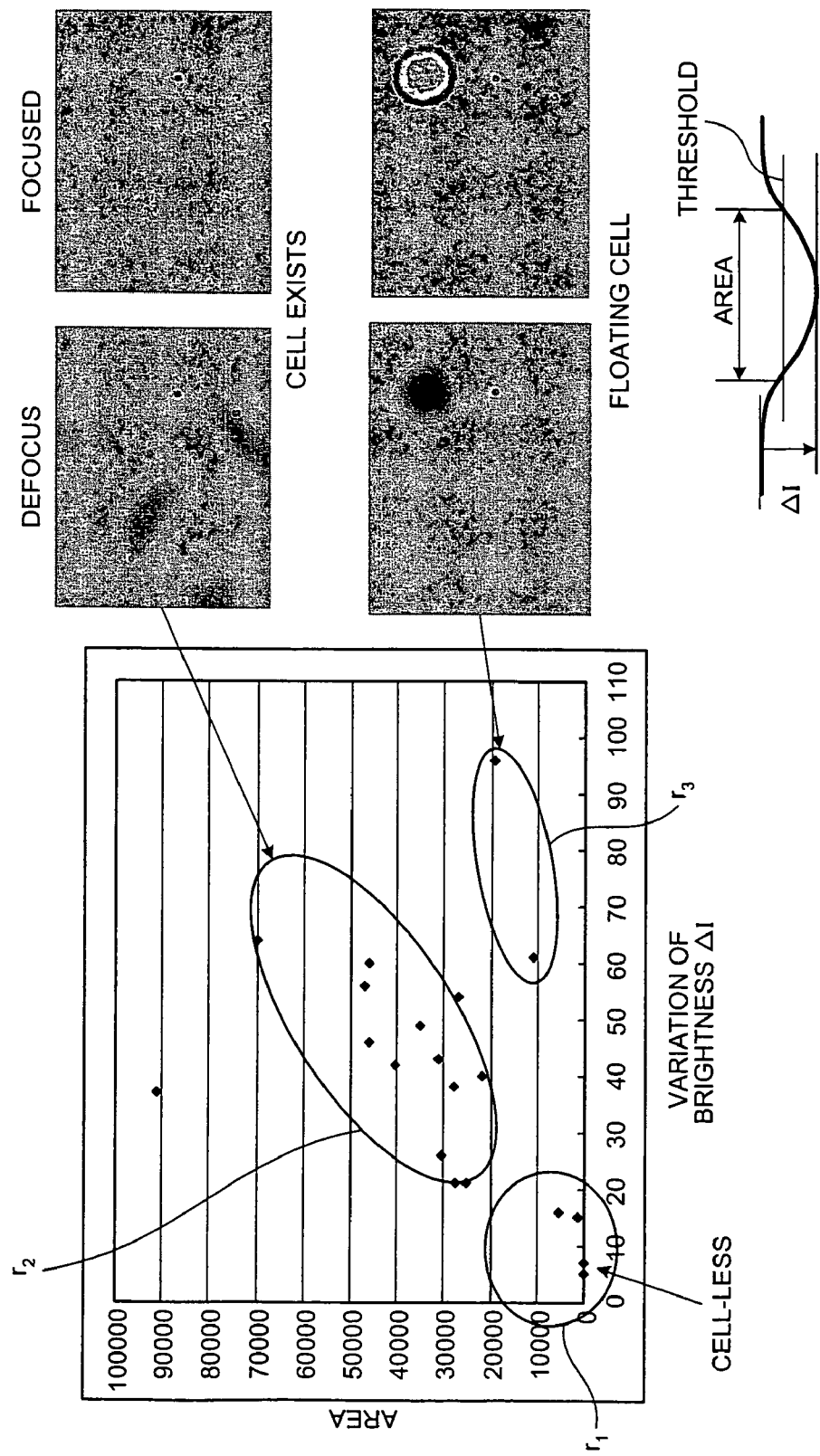
FIG. 6 is a schematic explaining how the judgment whether a cell is present is made.

Schematic description will now be made of a cell presence judgment in the needle position adjustment method according to the embodiment. FIG. 6 is a schematic for explaining the cell presence judgment in the needle position adjustment method according to the embodiment. In the needle position adjustment method, firstly illumination is irradiated on the adherent cell from an illumination source arranged above the adherent cell adhering to the base surface of the petri dish, a focal position of the objective lens against the adherent cell on the base surface is located at a position away from the adherent cell, and a defocused image is obtained by taking the defocused image of the adherent cell with the CCD camera through the objective lens arranged below the base surface, in an automatic focal point adjustment method.

Prior to this defocused image, a defocused image is taken with the focal point set 1 mm above the petri dish. This is determined as a standard reference image. Though this reference image is considerably blurred as compared with the defocused image with the focal point set at a position close to an expected surface position of the adherent cell, these two defocused images have approximate distributions of intensity of light from the illumination source, and a height variation due to a slope of the base surface of the petri dish is 100 μm to 200 μm at best, small enough as compared with 1 mm, making no big difference to the image characteristics, and therefore, the reference image can be used as the reference image in respect of brightness of the image.

Figure 7A:
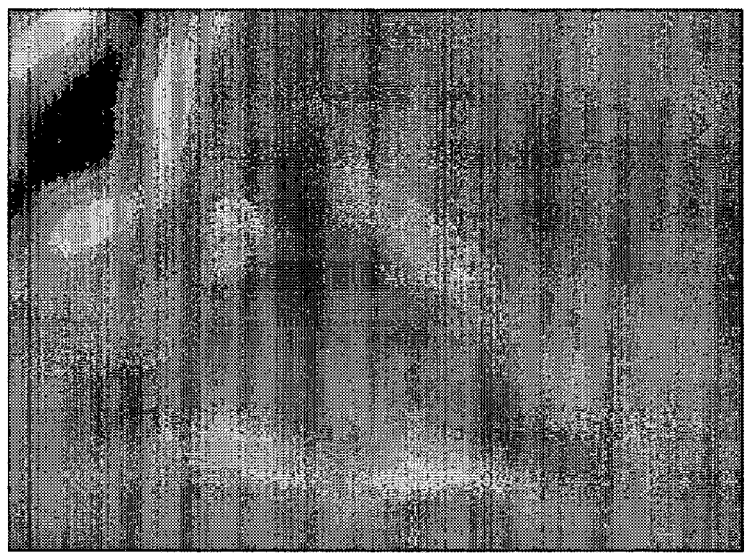
FIGS. 7A to 7D are images of a cell.

Next, a defocused image is taken with the focal point set at the focal position 200 μm above the adherent cell, and an image of difference from the reference image is obtained. Or, defocused images are taken with the focal point set at a plurality of different positions, at positions close to the expected surface position of the adherent cell, and images of difference from the reference image are obtained. A slice level determining a plurality of different positions for the focal point is to be a brightness value 10% to 20% smaller than that of the reference image. FIG. 7A is a diagram of a sample of the defocused image obtained by this processing.

Figure 7B:

Out of the defocused image with the focal point set at the focal position 200 μm above the adherent cell or the defocused images taken at the slice level, the image in which the adherent cell is present has a region with a low brightness and a dark look as compared with a surrounding region. At a part where the adherent cell is not present, the brightness is little different from that of the reference image. Out of the difference images, the difference image in which the adherent cell is present is binarized. Digitizing is a processing of expressing an image in monochrome; the processing of converting each pixel to white if the brightness of such pixel is greater than a predetermined threshold and converting each pixel to black if the brightness of such pixel is smaller than the predetermined threshold. FIG. 7B is a diagram of a sample of the defocused image binarized by this processing.

Referring to the difference image with the binarized adherent cell, an area of a region whose brightness is lower than that of a surrounding region, and at the same time, the smallest brightness value in such region can be obtained. The lower brightness than that of a surrounding region unit that the brightness is smaller than a predetermined threshold. If a correlation between the area and the brightness is in a certain relationship, it can be judged that a normal adherent cell that can be an object of microinjection is present within the visual field of the objective lens in which the defocused image is taken. The region in which the cell is not present can be identified by the correlation between the area and the brightness of the region whose brightness is lower than that of the surrounding region.

For example, in a graph of a correlation in FIG. 6, points specified by ΔI showing a degree of lowness of brightness from a standard, with the brightness of the reference image being taken as the standard, and by an area of the region whose brightness is lower than a predetermined threshold are plotted on a two-dimensional correlation graph. If a plotted point is present in the region illustrated as r1, then it can be judged that the adherent cell itself is not present within the visual field of the objective lens in which the defocused image is taken.

If a plotted point is present in the region illustrated as r2, then it can be judged that a normal adherent cell that can be an object of microinjection is present in moderate concentration within the visual field of the objective lens in which the defocused image is taken. If a plotted point is present in the region illustrated as r3, then it can be judged that since a normal adherent cell that can be an object of microinjection is present in a floating condition within the visual field of the objective lens in which the defocused image is taken, the adherent cell can not be used for the microinjection.

Figure 7C:
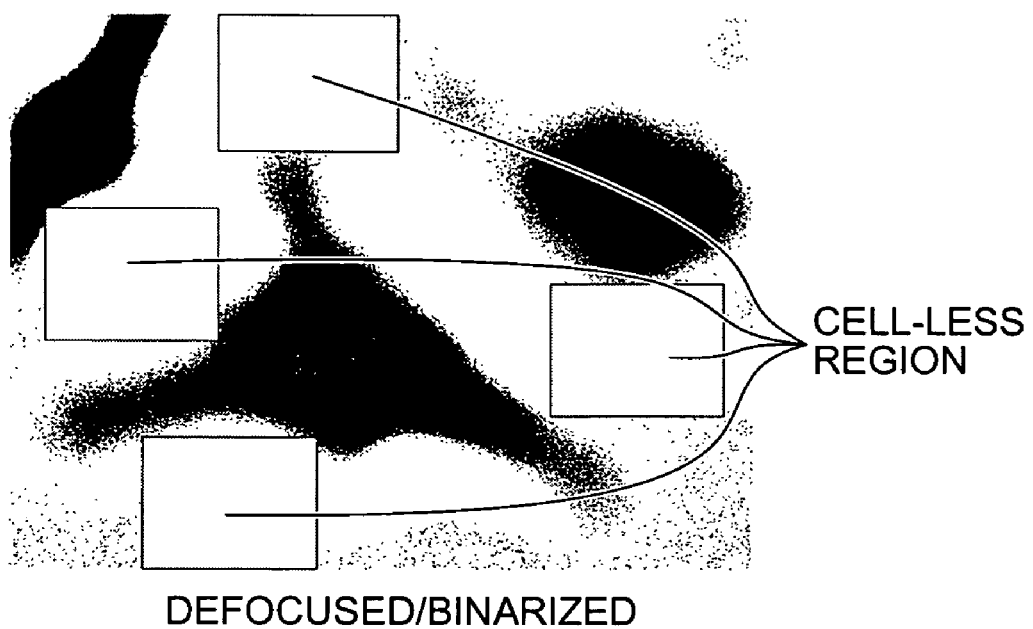

Out of the binarized defocused images as to which presence or absence of the cell is judged in the above-identified processing, a certain region within which the cell is not present is searched. Namely, in the defocused image as to which the judgment is that the cell is present, a blank region in which the cell is not present is searched. FIG. 7C is a diagram of a cell-less region being searched in the defocused image by this processing.

Figure 7D:
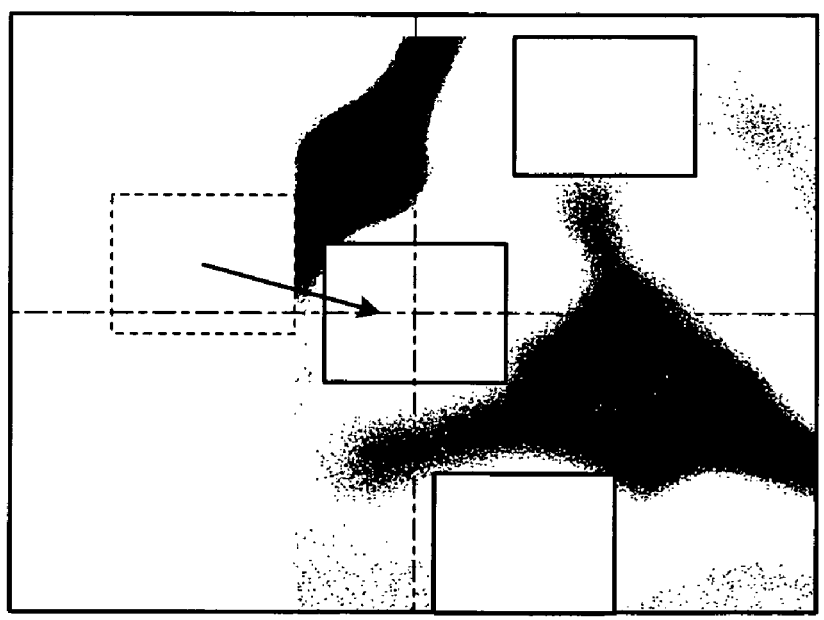

Furthermore, to obtain a background image of a needle image, one of the cell-less regions found in the defocused image as to which judgment is that the cell is present is shifted to the center of the visual field of the objective lens. Then, when the cell-less region is shifted to the center of the visual field of the objective lens, a background image is taken. FIG. 7D is a diagram of the cell-less region being shifted to the center of the image.

Figure 8:
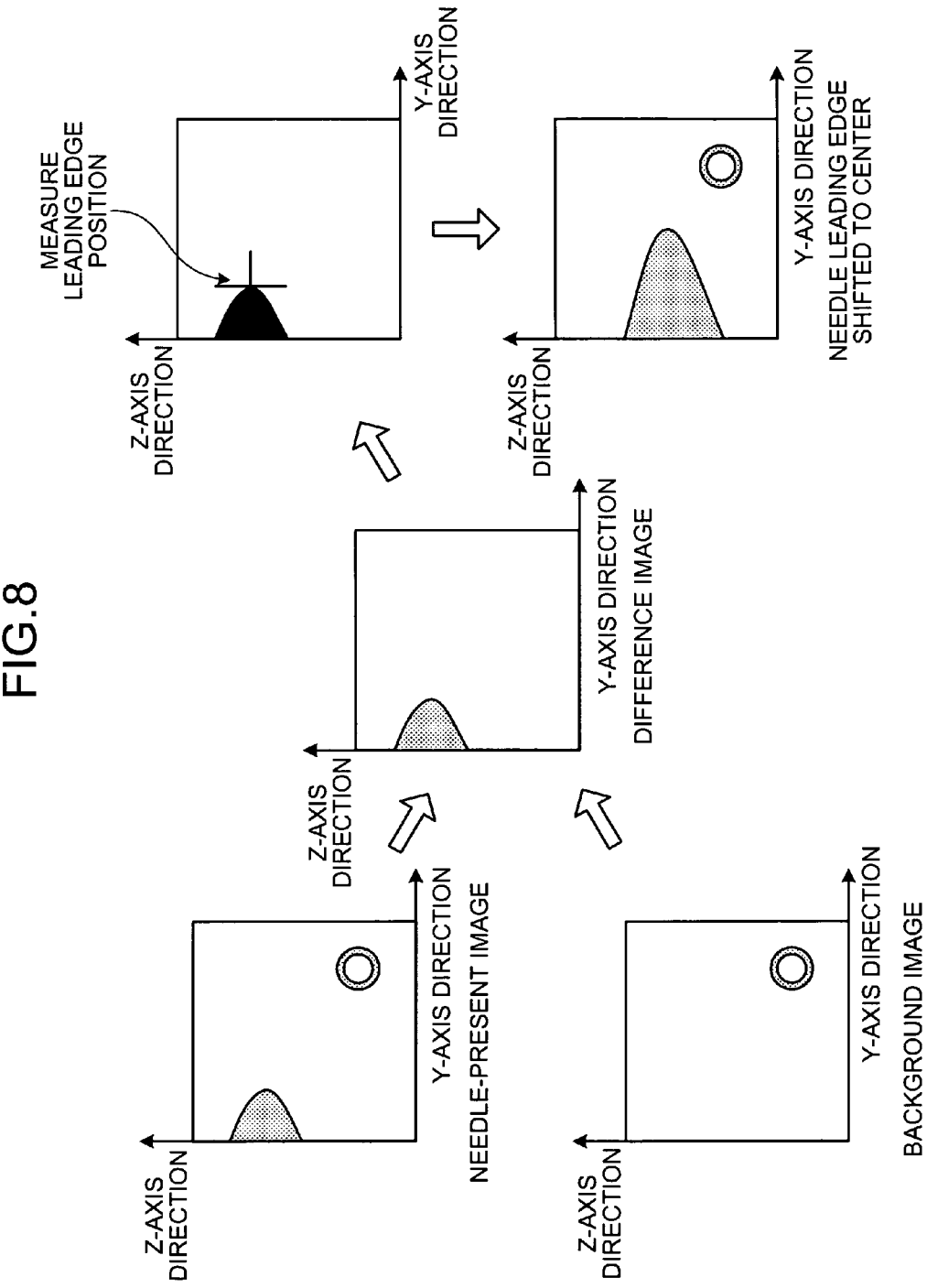
FIG. 8 is a schematic for explaining the needle detection processing.

Schematic description will then be made of a needle detection processing according to the embodiment. FIG. 8 is a schematic for explaining the needle detection processing according to the embodiment. As shown in FIG. 8, after taking a background image, the position of the leading edge of the needle is shifted to within an observation region, based on a predetermined parameter (for example, the information on a material of the petri dish) and an image is taken. This image is referred to as a needle-present image. At this stage, the leading edge of the needle is not in contact with the focal plane.

A difference image of the needle-present image and the background image is then obtained and image noises (such as small dusts, shadow of the cell, etc.) present within the image field are deleted. If the needle is within the image field, then the region of the needle is detected as a shadow. This difference image is binarized and the position of the leading edge of the needle is measured. Based on results of the measurement, the leading edge of the needle is shifted to the center of the image field. If the needle is not detected within the image field, then the search continues until the image of the leading edge of the needle is detected, by shifting the petri dish stage in horizontal direction.

Figure 10A:
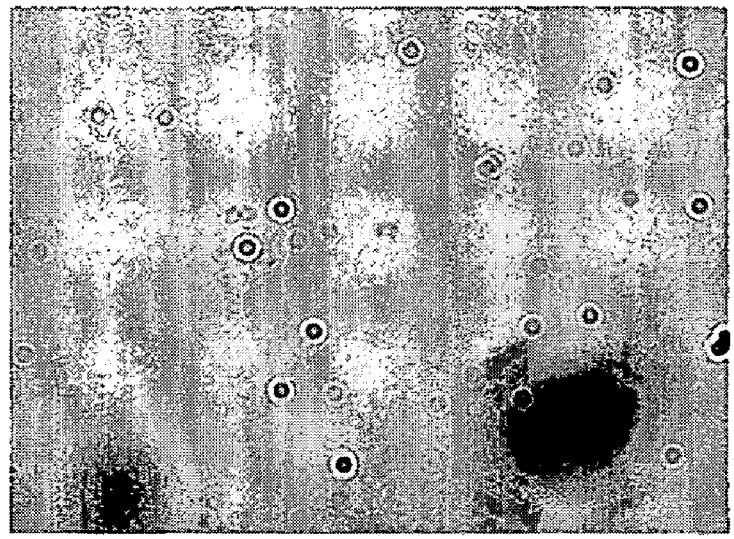
FIGS. 10A to 10D are images of a needle.
Figure 10B:
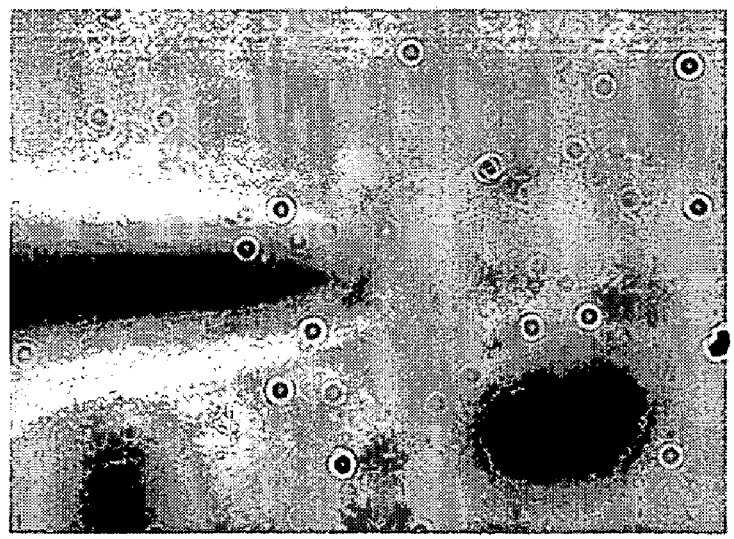
Figure 10C:
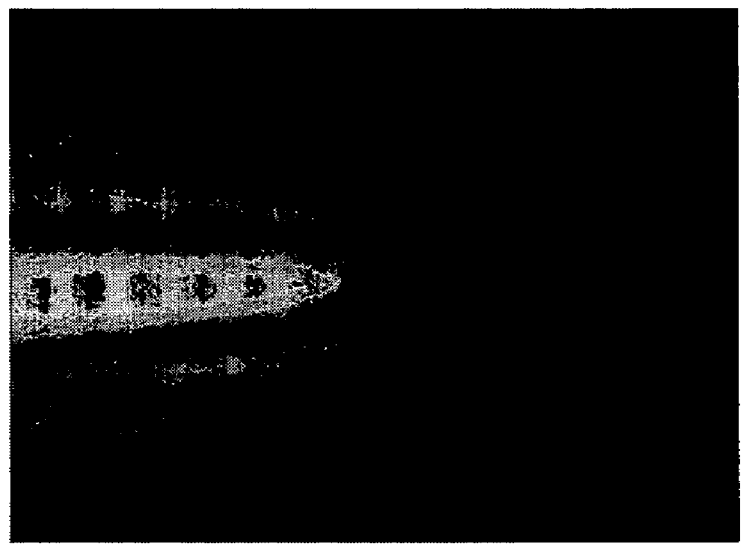
Figure 10D:
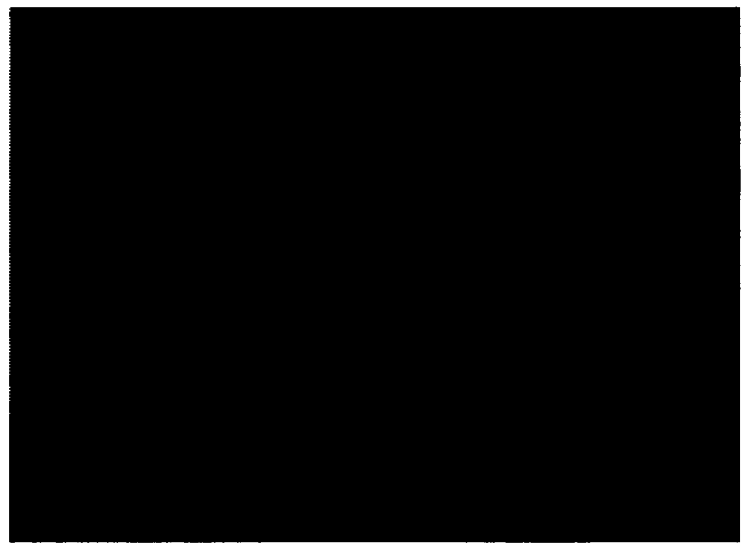

Schematic description will then be made of an image processing in the needle detection processing according to the embodiment. FIG. 9 is a schematic for explaining the image processing in the needle detection processing according to the embodiment. As shown in FIG. 9, using the same method as shown in FIG. 8, the difference image of the needle-present image and the background image is obtained and this difference image is then binarized. Furthermore, a differential processing is applied to the binarized difference image by the method such as Sobel processing. The differential-processed image is referred to as a differential image. The differential processing calculates a differential aggregate by aggregating absolute values of differential values for each image. FIG. 10A shows an example of the background image. FIG. 10B shows an example of the needle-present image. FIG. 10C shows an example of the difference image. FIG. 10D shows an example of the differential image.

Schematic description will then be made of a difference image judging method in the needle detection processing according to the embodiment. FIG. 11 is a schematic for explaining the difference image judging method in the needle detection processing according to the embodiment. FIG. 1b is a diagram showing how a differential value and an approximate shape thereof relate to a height position of the needle. The differential value, whether the image is blurred with the needle positioned above the focal plane or the image is blurred with the needle positioned below the focal plane, appears as equally small image, and there is no big difference. In the embodiment, the case of blurring with the needle positioned above the focal plane is referred to as an upper blur and the case of blurring with the needle positioned below the focal plane is referred to as a lower blur.

However, when the needle comes close to the focal plane, the differential aggregate becomes great. On the other hand, when looking at the characteristics of blurred images, in the case of the upper blur, the image is shaped to narrow at the right side (right narrowing). It is understood that the needle runs from the upper left to the lower right. In the case of the lower blur, the image is large at the right side and is shaped to narrow at the left side (left narrowing). Near the focal point of the needle, the shape near the focal point is complicated.

As a method of finding the position of the needle from these characteristics, the differential aggregate is firstly obtained, and if the differential aggregate is lower than a certain value, then it is judged as the upper blur or the lower blur. When it is either the upper blue or the lower blue, then a judgment is made as to whether it is the upper blur or the lower blur. According to such judgment, the needle is shifted to approach the focal position. Lastly, at the time when the differential aggregate becomes greater than a certain value, a precision calculation is made again. By this method, the needle can be brought closer toward the focal point.

Figure 12A:
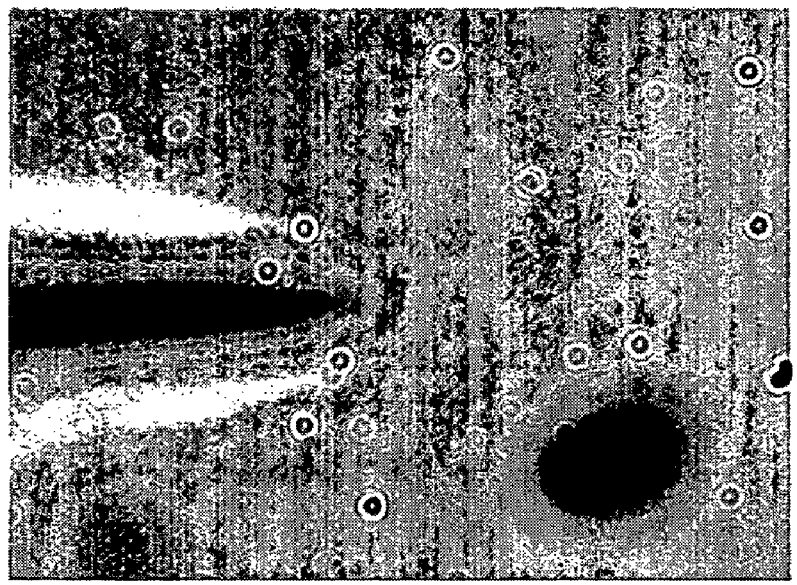
FIGS. 12A to 12D are difference images.
Figure 12B:
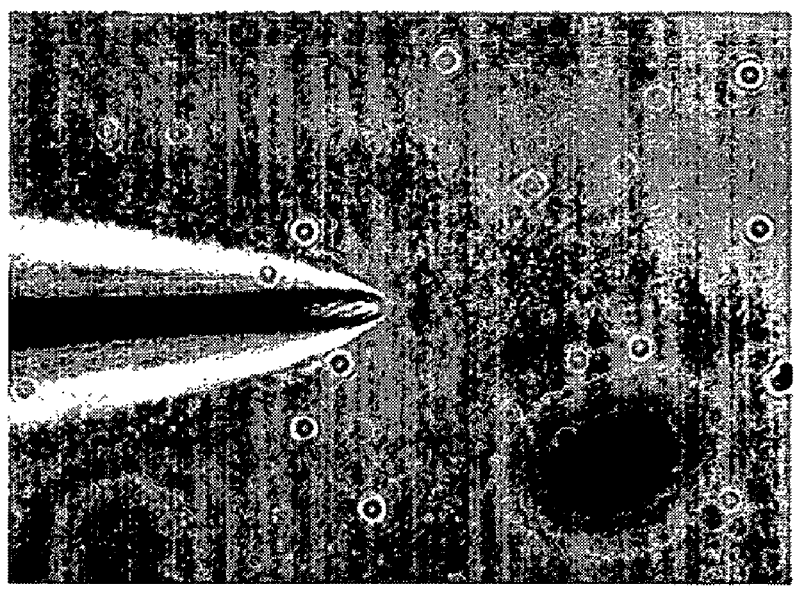
Figure 12C:
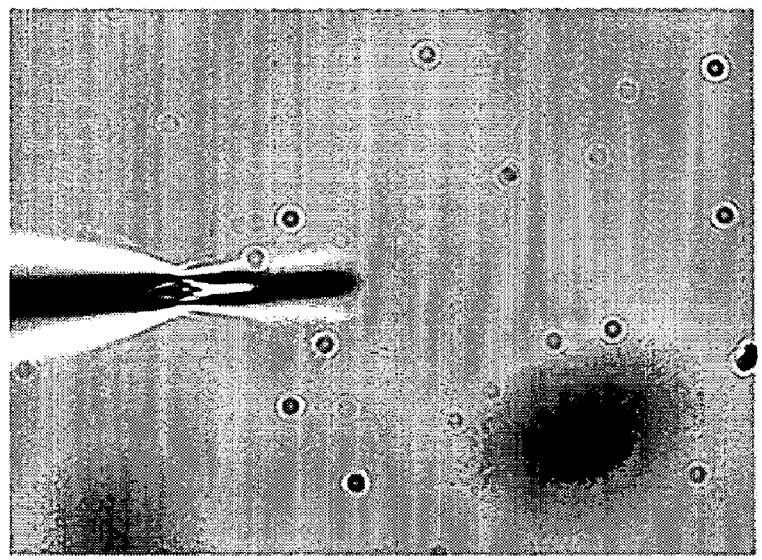
Figure 12D:
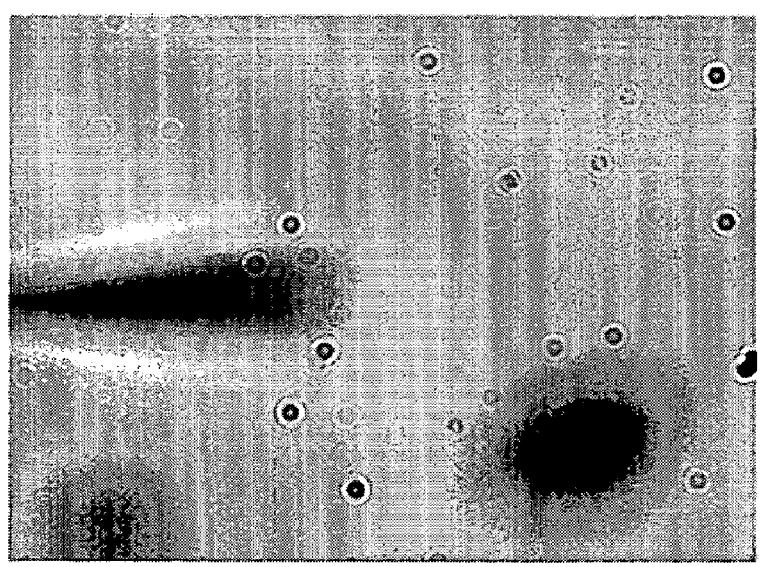

FIG. 12A shows an example of an image in the case of the upper blur. In this case, the leading edge of the needle is positioned 100 μm above the focal plane. FIG. 12B shows an example of a focused image. In this case, the leading edge of the needle is in contact with the focal plane. FIG. 12C shows an example of the image when the leading edge of the needle is slightly below the focal plane. In this case, the leading edge of the needle is positioned 20 μm below the focal plane. FIG. 12D shows an example of an image in the case of the lower blur. In this case, the leading edge of the needle is positioned 100 μm below the focal plane.

Figure 13:
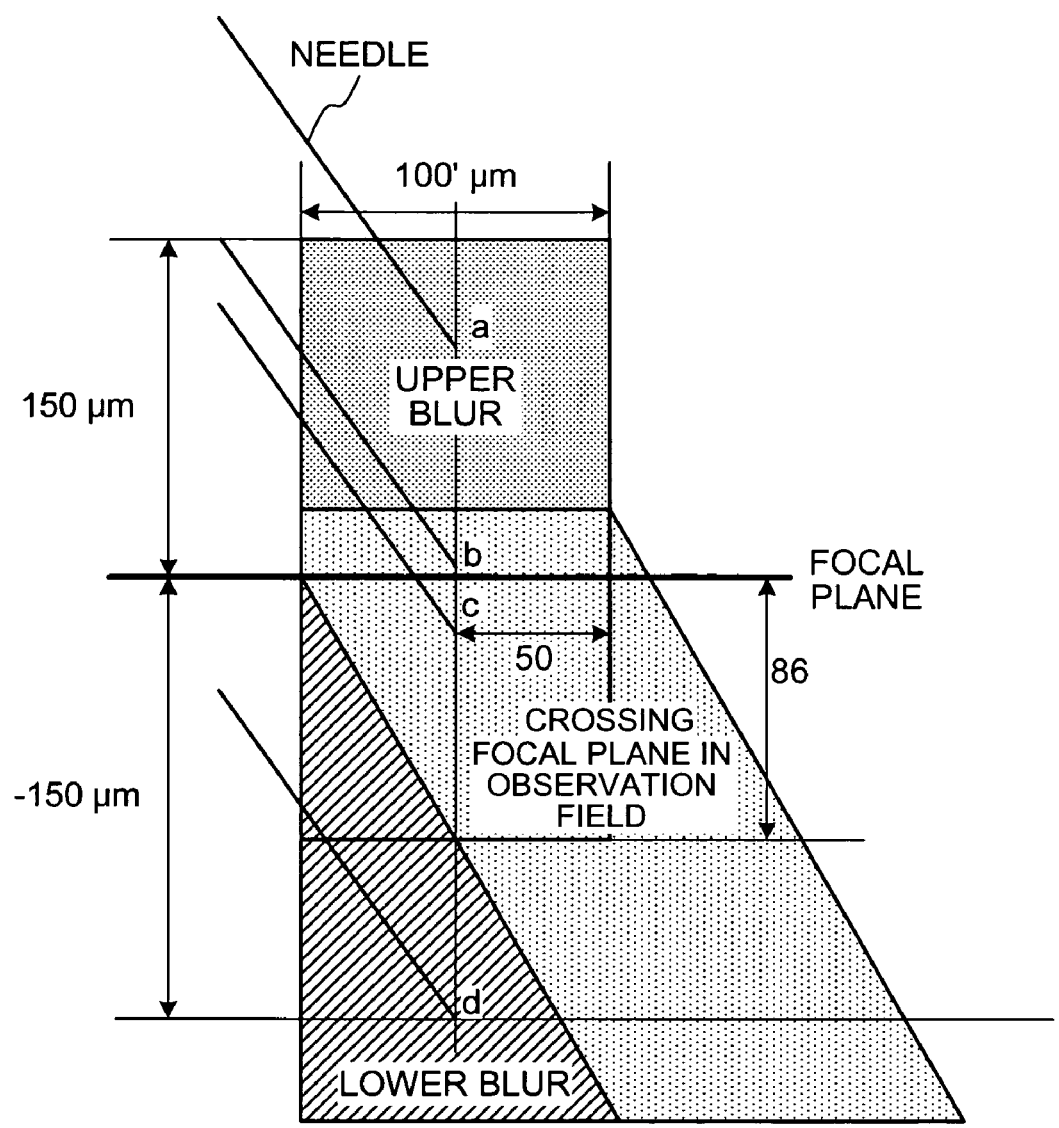
FIG. 13 is a schematic for explaining the correlation between the needle position and the blur.

Description will now be made of the correlation between the needle position and blur in the needle detection processing according to the embodiment. FIG. 13 is a diagram of the correlation between the needle position and the blur in the needle detection processing according to the embodiment. FIG. 13 shows the relationship between the needle position and errors when same petri dish is used.

In case of an observation area size (horizontal distance) being 100 μm, when the needle is below the focal plane, a part of the needle crosses the focal plane. However, when the needle is above the focal plane, the needle radically becomes blurred. Here, the blur at the upper part is called an upper blur (when the needle is at the position a) and the blur at the lower part is called a lower blur (when the needle is at the position d). When the leading edge of the needle meets the focal plane (when the needle is at the position b), it is called "focused", and when the needle crosses the focal plane (when the needle is at the position c), it is called "partially focused". When the vertical position of the needle is at the regions to which the needle positions of a to d belong, the image becomes the upper blur, focused, partially focused, and the lower blur, respectively.

Figure 14:
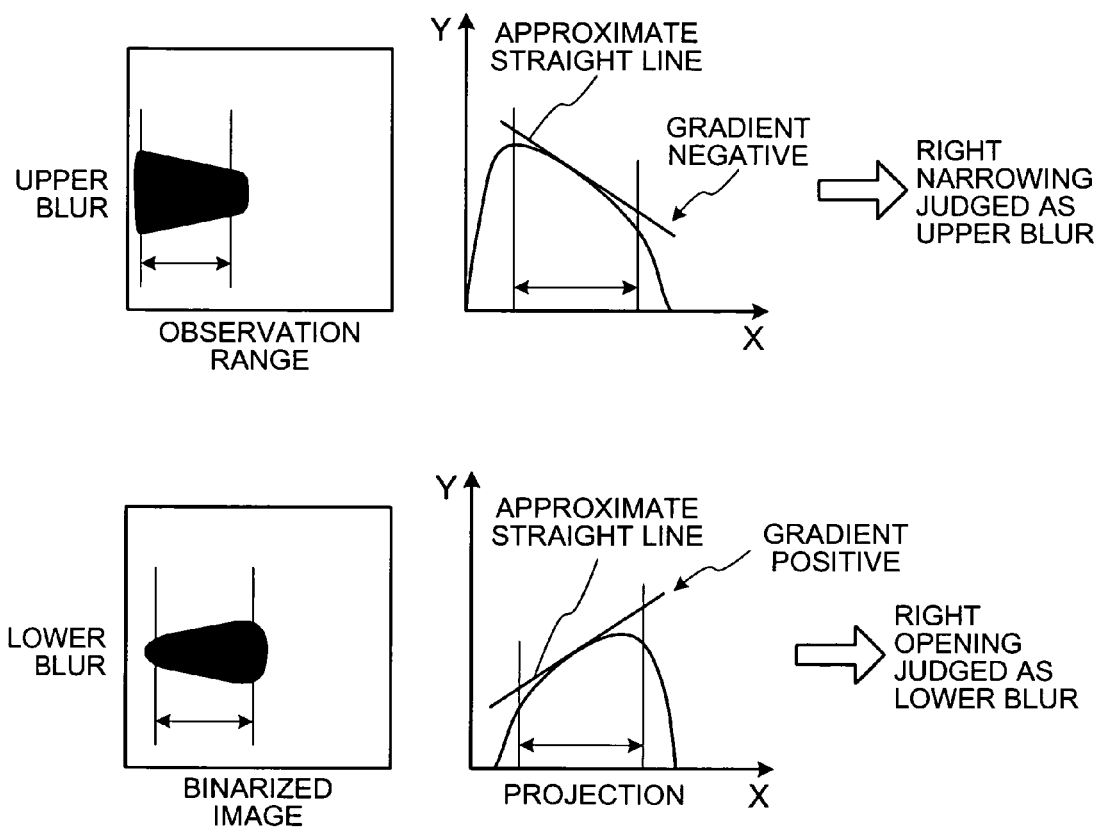
FIG. 14 is a schematic for explaining the needle position polarity detection processing.

Schematic description will then be made of the needle position polarity detection processing according to the embodiment. FIG. 14 is a schematic for explaining the needle position polarity detection processing according to the embodiment. FIG. 14 is a diagram of a specific example of the needle blur judgment method based on the shape.

After the difference image of the needle is binarized, the image is projected in the X-axis direction. As a result, a transition characteristics curve of the image width in Y direction against the position in X direction is obtained. This shows a change of shape of the needle in X-axis direction. As a judging method, calculation is made of an approximate straight line of the characteristics obtained by cutting out a middle part of the characteristics, removing the information around the origin and around the leading edge of the needle, and a gradient thereof is found. The approximate straight line may be a tangent to the transition characteristics curve at a point belonging to the cut-out middle part, or may be a straight line connecting two terminal points of the middle part of the transition characteristics curve. When the gradient is negative, the image is judged as the upper blur and when the gradient is positive, the image is judged as the lower blur.

Figure 15:
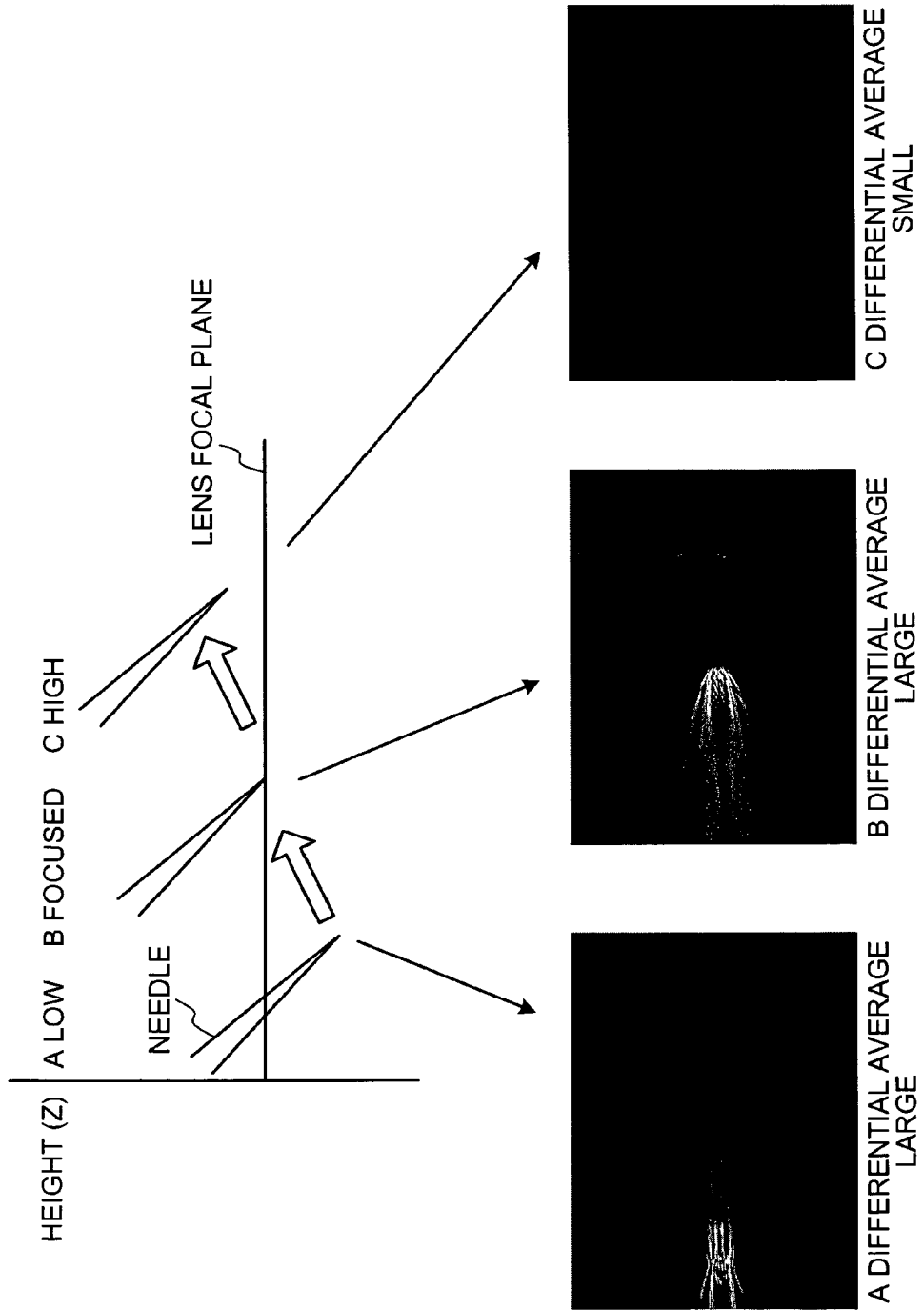
FIG. 15 is a schematic for explaining the needle position precision adjustment processing.

Schematic description will then be made of the needle position precision adjustment processing according to the embodiment. FIG. 15 is a schematic for explaining the needle position precision adjustment processing according to the embodiment. FIG. 15 is a diagram describing a method of finding a more accurate focal position when the differential aggregate value becomes greater than a certain value and the needle comes close to the focal plane.

Used here is the property that the differential average is great when the leading edge of the needle is below the focal plane, but the value radically becomes small when the leading edge is above the focal plane. The upper half of FIG. 15 shows the height of the needle and the lower half shows the differential images corresponding to respective height positions.

The differential average comes to the maximum when a part of the needle crosses the focal plane. These differential images show that the differential average is great when the leading edge of the needle is in contact with the focal plane or is below the focal plane (at the needle position A or B), but that the differential average becomes small when the leading edge of the needle is above the focal plane (at the needle position C). Therefore, by finding the point of radical change of the differential value, accurate focal plane position can be measured.

Figure 16:
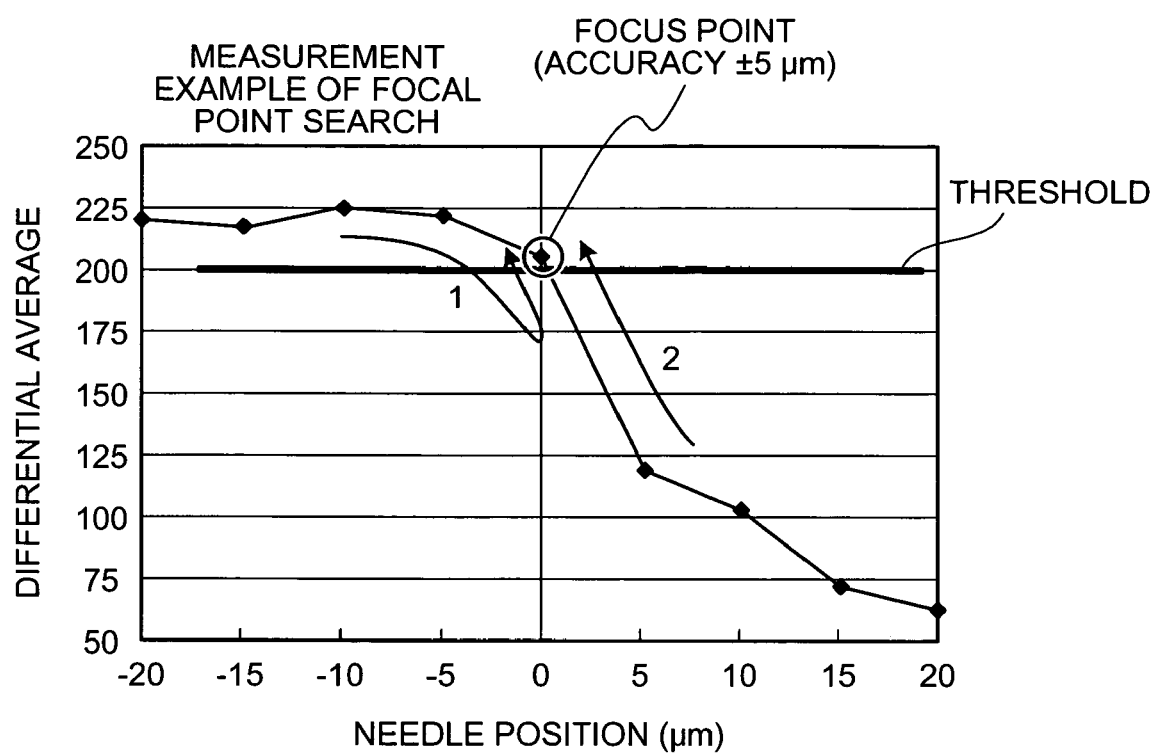
FIG. 16 is a schematic for explaining a processing example of a focal point search in the needle position precision adjustment processing.

Schematic description will then be made of a processing example of a focal point search in the needle position precision adjustment processing according to the embodiment. FIG. 16 is a schematic for explaining a processing example of a focal point search in the needle position precision adjustment processing according to the embodiment. FIG. 16 shows data for the focal point detection of the focal point search in the needle position precision adjustment processing. A left half of a curve connecting the plotted dots shown in FIG. 16 shows the case where the leading edge of the needle is below the focal plane, and a right half of the curve shows the case where the leading edge of the needle is above the focal plane. A vertical axis indicates the differential average when the differential aggregate is a value greater than a certain value. Since the differential value itself largely varies and the maximum value thereof alone is not enough to stabilize the data, the differential average is used for stabilizing the data by averaging.

By setting a threshold in FIG. 16, the focal position can be judged. Namely, when the leading edge of the needle is below the focal position (the case shown by the arrow 1 in the Figure), the differential average is great. In this case, the needle is gradually lifted upward, and by supposing that when the differential average becomes smaller than the threshold, the focal point is passed, the position one step backward is judged as the focused position.

On the other hand, when an original position of the needle is above the focal plane (the case shown by the arrow 2), the differential average is smaller than the threshold. In this case, the needle is gradually lowered, and the position at which the differential average exceeds the threshold is judged as the focused position. In this manner, the position of the leading edge of the needle and focal plane can be brought to correspond with each other, with around ±5 μm accuracy.

Figure 17:
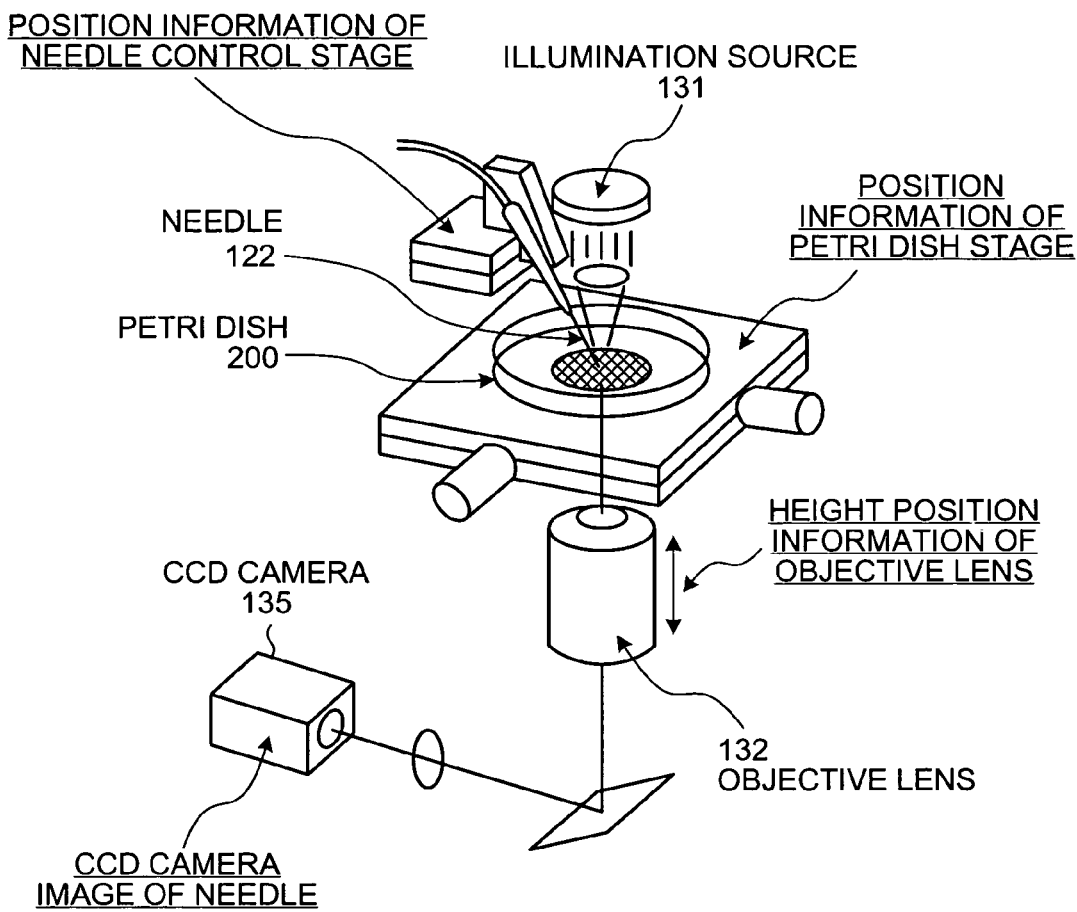
FIG. 17 is a schematic for explaining information input into the microinjection apparatus.

Description will then be made of input information into the microinjection apparatus in the automatic focal point adjustment method according to the embodiment. FIG. 17 is an explanatory diagram for description of input information into the microinjection apparatus in the needle position automatic adjustment method according to the embodiment. As shown in FIG. 17, the information input into the microinjection apparatus includes the position information of the petri dish stage indicating the visual field position information of the objective lens 132 in the petri dish stage on which to put the petri dish 200; the position information of the needle control stage indicating the needle control position in the needle control stage for controlling the operation of the needle 122 for the injection; the height position information of the objective lens 132 that is the information on the shift position for shifting the objective lens 132 for measuring the focal point of the adherent cell on the bottom surface of the petri dish; and the CCD camera image of the needle that is the image of the leading edge of the needle. Based on such information input into the microinjection apparatus, the output information shown in FIG. 18 can be obtained.

Figure 18:
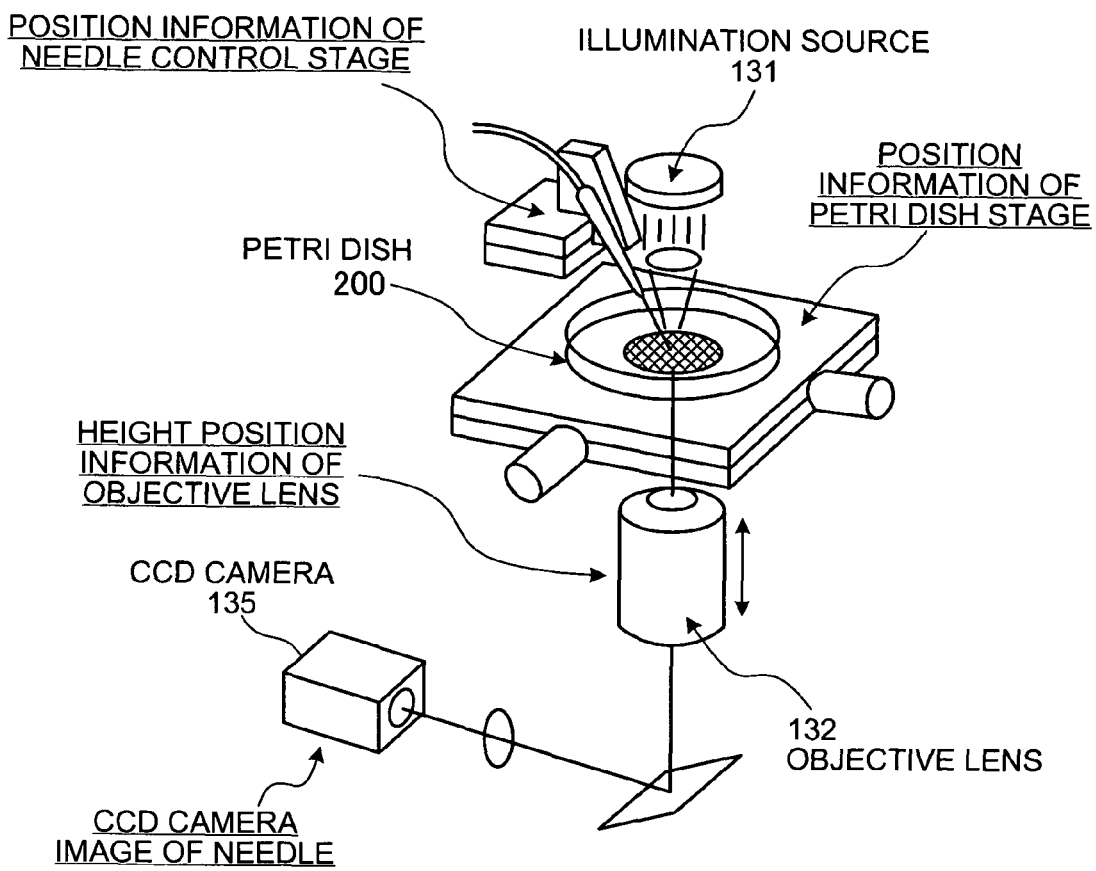
FIG. 18 is a schematic for explaining information output from the microinjection apparatus.

Description will then be made of output information from the microinjection apparatus in the automatic focal point adjustment method according to the embodiment. FIG. 18 is an explanatory diagram for description of output information from the microinjection apparatus in the needle position automatic adjustment method according to the embodiment. As shown in FIG. 18, the information output from the microinjection apparatus includes the position control information of the needle control stage indicating the position as a result of the control of the needle in the needle control stage for controlling the operation of the needle 122 for the injection; the position information of the petri dish stage indicating the results of control of the visual field position information of the objective lens 132 in the petri dish stage on which to put the petri dish 200; the height position information of the objective lens 132 indicating the focal position of the needle measured for causing the height of the needle to correspond to the cell surface; the defocused image of the needle; the binarized version of this defocused image; and the CCD camera image of the needle such as focused image.

Figure 19:
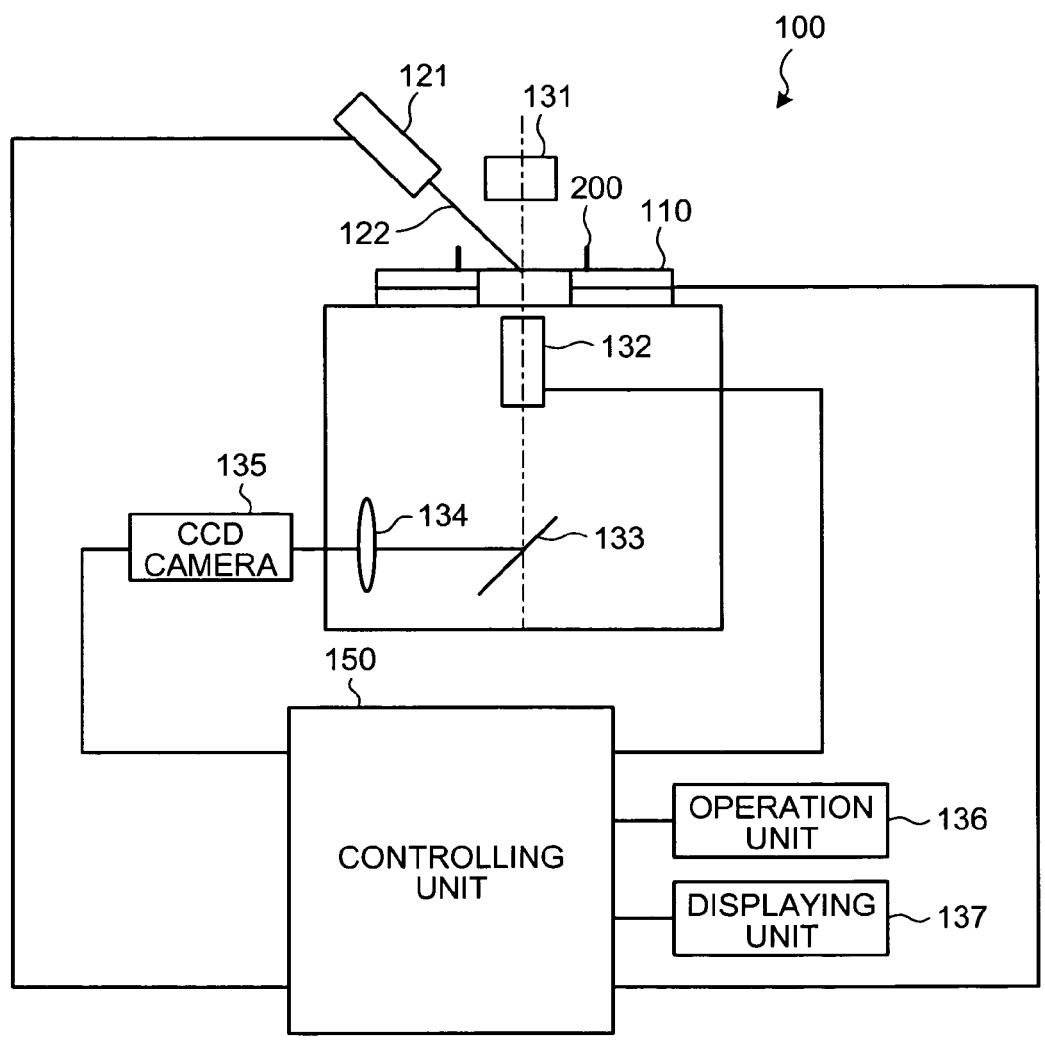
FIG. 19 is a schematic of the microinjection apparatus.

Description will then be made of configuration of the microinjection apparatus according to the embodiment. FIG. 19 is a functional block diagram of the configuration of the microinjection apparatus according to the embodiment. As shown in FIG. 19, the microinjection apparatus 100 includes the petri dish stage 110, the injector 121, the needle 122, the illumination source 131, the objective lens 132, the reflector 133, the focusing lens 134, the CCD (charge coupled devices) camera 135, the operation unit 136 for inputting, etc. of the search parameters and petri dish information, the displaying unit 137, and the controlling unit 150.

The petri dish stage 110 is an X-Y stage movable in horizontal direction and serves as a table for holding the petri dish 200. On the petri dish stage 110, the petri dish 200 can be pressed and fixed by a force of a spring sideways. In this manner, the petri dish 200 and the petri dish stage 110 are unified as one unit, and therefore, the shifting of an observation position of the bottom surface of the petri dish for searching the adherent cell present on the bottom surface inside the petri dish corresponds with the shifting of the observation position by shifting the petri dish stage 110. The injector 121 is an apparatus for moving the needle 122 upward or downward or injecting a gene filled within the needle 122, based on the control of the control stage 150. The needle 122 is a capillary, glass needle with a miniaturized leading edge.

The illumination source 131 is a light source to illuminate an object of injection from above, and the objective lens 132 is a lens for obtaining a magnified image of an object of injection from below the petri dish 200. The reflector 133 is a mirror for reflecting the image obtained by the objective lens 132 toward the focusing lens 134, and the focusing lens 134 is a lens for focusing an image on an imaging device of the CCD camera 135.

The CCD camera is a means for converting an optical image to an electronic image data, using the imaging device, and it transmits the converted electronic image to the controlling unit 150.

The controlling unit 150 is a controlling unit in charge of an overall control of the microinjection apparatus 100, and performs the processing of contact detection of the needle 122 and the base surface and the injection automatic execution processing, etc. Operation unit 136 is means for accepting the input of processing instructions and setting information necessary for the controlling unit 150 to carry out various processing. The displaying unit 137 is a means for accepting the input of instructions, etc. from users and displaying various information, and consists of a keyboard, display, etc. The displaying unit 137 is also a means for displaying the information on the state of progress of various processing and the scanned images of the adherent cell resulting from various processing.

Figure 20:
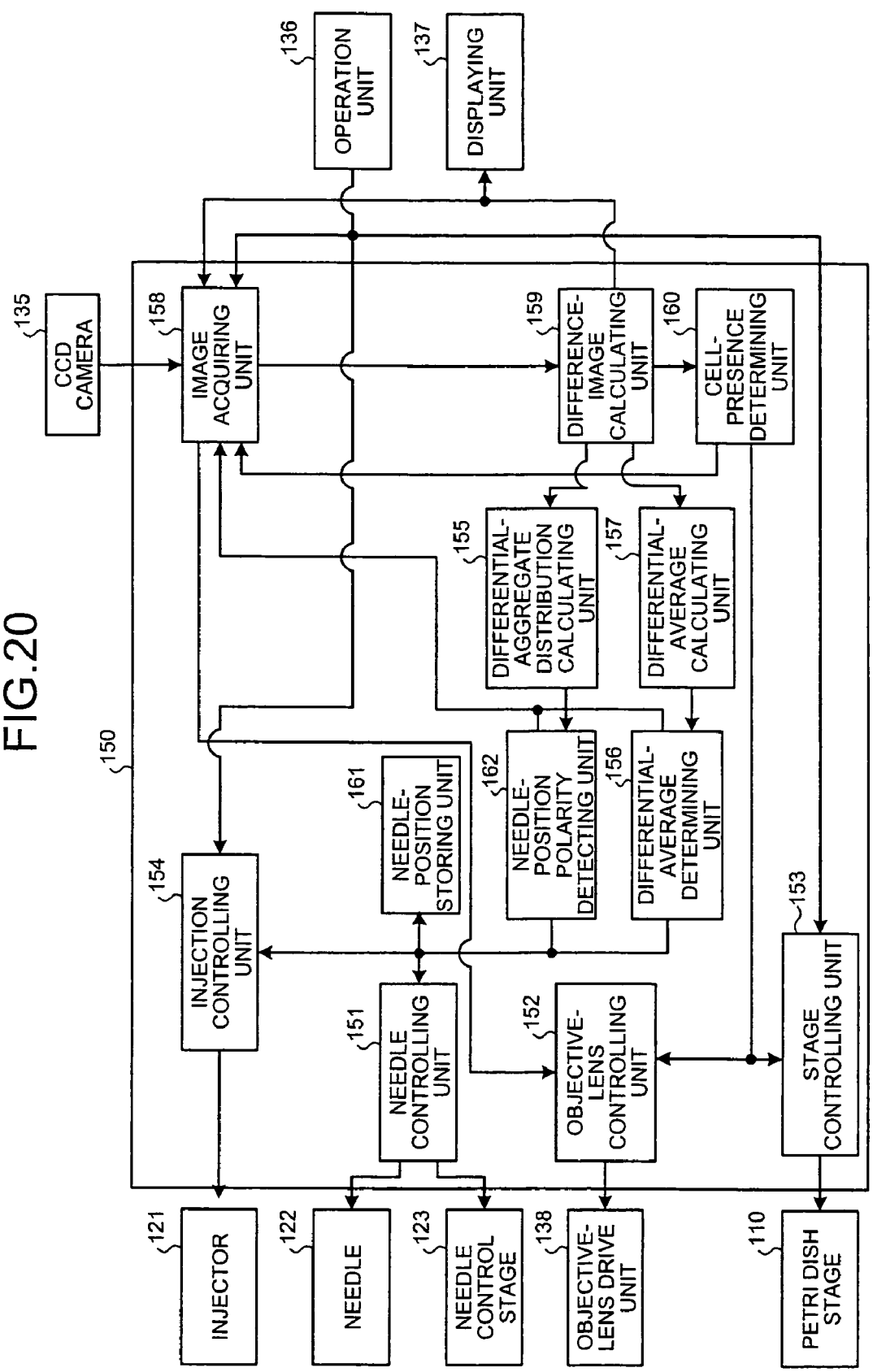
FIG. 20 is a detailed functional block diagram of the microinjection apparatus.

Description will then be made of configuration of the controlling unit of the microinjection apparatus according to a first embodiment. FIG. 20 is a functional block diagram of the configuration of the controlling unit of the microinjection apparatus according to the first embodiment. As shown in FIG. 20, the controlling unit 150 of the microinjection apparatus includes a needle controlling unit 151 controlling the drive of the needle 122 and the needle control stage 123, an objective-lens controlling unit 152 that changes the focal position of the objective lens by controlling the drive of an objective-lens drive unit 138, a stage controlling unit 153 that controls the drive of the petri dish stage 110, an injection controlling unit 154 that controls the injector 121, a differential-aggregate distribution calculating unit 155, a needle-position polarity detecting unit 162, a differential-average calculating unit 157, a differential-average determining unit 156, an image acquiring unit 158 that acquires the image from the CCD camera 135, a difference-image calculating unit 159, a cell-presence determining unit 160, and a needle-position storing unit 161.

The image acquiring unit 158, upon receipt of an instruction to start an automatic adjustment of a needle position at the adherent cell accepted at the operation unit 136 or signal input from the needle-position polarity detecting unit 162 or the differential average judgement unit 156, controls the objective-lens controlling unit 152 to set the CCD focal point at various focal positions input and set by the operation unit 136 in advance and to acquire the needle image from the CCD camera 135. The image acquiring unit 158 also transfers the reference image, the background image and images at a plurality of focal positions acquired after a sequence of processing to the difference-image calculating unit 159. The image acquiring unit 158 also outputs the needle images acquired in such processing to the displaying unit 137 for display.

Out of images at a plurality of focal positions, the image taken by setting the focal position, for example, 1 mm above the adherent cell is the reference image, and the image taken by setting the focal position 200 μm above the adherent cell is the image used for detecting the presence of the cell. The image taken at the region at which the cell is not present is the background image. Images taken by setting the focal point at other positions are the images to be used in the needle image acquisition processing (step S131, step S203 or step S211 to be described later).

The difference-image calculating unit 159 digitizes the reference image, the background image, and images at a plurality of focal positions transferred from the image acquiring unit 158, and calculates the difference image of two images. The difference image of the image taken by setting the focal point at the focal position 200 µm above the adherent cell from the binarized reference image is transferred to the cell-presence determining unit. The difference images of the images of the needle taken by setting the focal point at predetermined focal positions from the binarized background image are transferred to the differential-aggregate distribution calculating unit 155 and the differential-average calculating units 157. These images are output so that they can be displayed at the displaying unit 137.

The cell-presence determining unit 160, based on the difference image of the image taken by setting the focal point at the focal position 200 µm above the adherent cell from the binarized reference image, calculates the area of the region whose brightness is lower than the predetermined threshold and the minimum brightness in such region, and determines the presence or absence of the cell in the visual field, from the correlation of the area and the minimum brightness.

When the judgment is that the cell is present in the visual field, the cell-presence determining unit 160 detects the region in which the cell is not present of the image in the visual field and instructs the stage controlling unit 153 to start the drive of the petri dish stage 110 so that the center of the visual field is shifted to such detected region. The cell-presence determining unit 160 also instructs the image acquiring unit 158 to start the acquisition of the image of the cell-less region in which the cell is not present in the visual field. When it is not judged that the cell is present in the visual field, the cell-presence determining unit 160 instructs the stage controlling unit 153 to shift to the next observation site (observation position, observation point).

The result of the judgment of the cell-presence determining unit 160 is used not only for detecting the region in which the cell is not present in the image in which the cell is present, but also may be used for extracting a cell-less region even from the image of the visual field in which the adherent cell is perfectly absent or in which the adherent cell is dispersed and floating.

The differential-aggregate distribution calculating unit 155 differentiates the difference image transferred from the difference-image calculating unit 159 and calculates the aggregate of absolute values of such differential values as the differential aggregate and calculates the differential aggregate distribution that is a distribution of the differential aggregate according to the focal positions. The differential-aggregate distribution calculating unit 155 transfers thus calculated differential aggregate distribution to the needle-position polarity detecting unit 162.

The needle-position polarity detecting unit 162 detects the vertical position in vertical direction of the needle so that the value of the differential aggregate becomes the maximum in the situation in which the shape of the leading edge of the needle at the focal position narrows at the right, by the method shown in FIG. 14. The detected vertical position of the needle is transferred to the needle controlling unit 151. The needle controlling unit 151 controls the drive of the needle control stage 123 so that the needle 122 is shifted to the vertical position as transferred.

The differential-average calculating unit 157, based on the difference image of the image acquired by minutely adjusting the needle position near the needle position detected by the needle-position polarity detecting unit 162 from the background image, calculates the differential average of difference images. Thus calculated differential average is transferred to the differential-average determining unit 156.

The differential-average determining unit 156, based on the differential average as transferred, determines and determines the lowest needle position while the differential average exceeds the predetermined threshold, by the method described by referring to FIG. 16. The determined needle position is transferred to the needle-position storing unit 161 for memorization. The determined needle position is transferred to the needle controlling unit 151 and the needle control stage is controlled to shift the needle to the determined needle position in vertical direction. The needle position information stored at the needle-position storing unit is read out at the start of the next microinjection and is used for the needle position adjustment.

As described above, by memorizing the once determined needle position information, the needle position search processing can be omitted when same petri dish is used, and therefore, microinjection can be performed speedily. Namely, the vertical position of the needle at the time when the leading edge of the needle is judged to be in contact with the focal plane of the lens is memorized, discriminating the petri dishes, and therefore, by measuring and preparing beforehand the needle position at the start of the operation according to physical attributes and optical attributes such as kinds, thickness of bottom part differing from one petri dish to another, material of the petri dish and by using such memorized needle position at the start of the microinjection, the operation can be started without measuring the needle position at the start of the operation, with a low workload, accurately, and speedily.

Once the needle position in vertical direction is determined by the differential-average determining unit 156, a microinjection instruction is given to the microinjection controlling unit 154. The microinjection controlling unit 154, upon receipt of this instruction, automatically, or based on the injection operation instruction from the operation unit 136, controls the injector 121 to execute the microinjection.

The stage controlling unit 153, based on not only the instruction to shift to the next observation site, but also the operation instruction from the operation unit 136, shifts the petri dish stage to an appropriate observation site.

Figure 21:
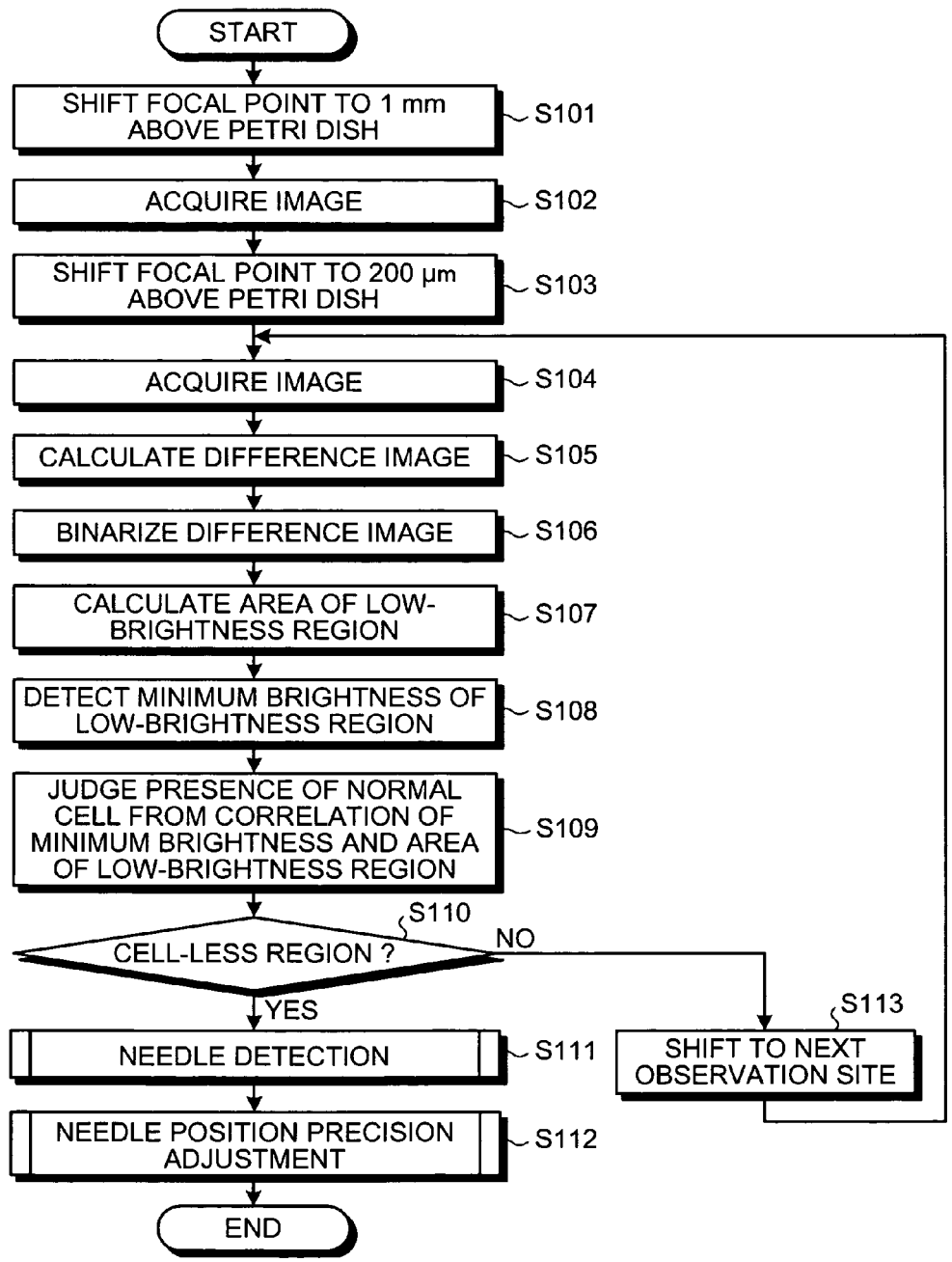
FIG. 21 is a flowchart of the needle position automatic adjustment processing procedure.

Description will then be made of a procedure of the needle position automatic adjustment processing performed in the microinjection apparatus according to the embodiment. FIG. 21 is a flowchart of procedure of the needle position automatic adjustment processing. As shown in FIG. 21, the focal position is shifted to the position 1 mm above the petri dish 200 (step S101), and an image as a reference image is acquired at this focal position (step S102). The focal position is shifted to the position 200 µm above the petri dish 200 (step S103), and an image is taken at this focal position (step S104).

The difference image is calculated of the reference image acquired at step S102 and the image acquired at step 104 (step S105), and the difference image is binarized (step S106). Calculation is made of an area of the low-brightness region whose brightness is lower than the threshold contained in the binarized difference image (step S107) and the minimum brightness in the low-brightness region is detected (step S108). Judgment is made of the presence or absence of a normal cell suitable for microinjection in the visual field, from the correlation of minimum brightness and the area of the low-brightness region (step S109).

Judgment is made as to whether a cell-less region is detected (step S110) and if the judgment is that the cell-less region is detected (Yes at step S110), then the needle detection processing (step S111) and the needle position precision adjustment processing (step S112) are executed. The procedure of the needle detection processing and the needle position precision adjustment processing will be described in detail later.

At step S110, if it is not judged that the cell-less region is detected in the visual field (No at step S110), then the process goes to the step S113. At step S113, the petri dish stage 110 is controlled and driven to be shifted to a next observation site. If the step S113 is finished, the process goes to the step S104.

Execution of such sequence of processing makes it possible to automatically search for an observation point at which the adherent cell is not present within the visual field of the objective lens 132, to detect the needle at this observation point and, if the needle is detected, to make a precision adjustment of the needle position. Namely, there is no need for the trial and error of manually shifting the vertical position of the needle 122 and manually adjusting so that the leading edge of the needle corresponds with the focal plane of the objective lens 132 at the adherent cell, and the needle position can be adjusted without complicated work and more accurately and the operation of the microinjection can be performed more efficiently. Furthermore, the automatic execution of the above-identified sequence of processing permits a reduction of psychological burden and psychological fatigue by a possible breakage of the needle 122 at the time of microinjection.

The needle detection processing procedure will then be described. FIG. 22 is a flowchart of details of the needle detection processing procedure shown in FIG. 21. As shown in FIG. 22, firstly, the cell-less region is shifted to the center of the visual field (step S121), the background image is acquired (step S122), and the needle is shifted to the minute adjustment position (step S123).

A needle image is acquired (step S124), a difference image is acquired of the needle image and the background image (step S125), and the difference image is binarized (step S126). Judgment is made as to whether the needle is present within the visual field (step S127). If the judgment is that the needle is present (Yes at step S127), then the position of the leading edge of the needle is detected (step S128), and the leading edge of the needle is shifted to the center of the visual field (step S130). If the step S130 is finished, then the process goes to the step S131.

On the other hand, if it is not judged that the needle is present within the visual field (No at S127), the needle position is shifted (step S129). If the step S129 is finished, then the process goes to the step S122.

At step S131, a needle image is acquired and a difference image is acquired of the needle image and the background image in the visual field acquired at the step S122 (step S132). Then, a differential aggregate of the difference image is calculated (step S133).

Judgment is then made as to whether the differential aggregate of the difference image exceeds the threshold (step S134). If it is judged that the differential aggregate exceeds the threshold (Yes at step S134), then the needle detection processing is finished and the process goes to the step S112 of the needle position automatic adjustment processing (FIG. 21). On the other hand, if it is not judged that the differential aggregate of the difference image exceeds the threshold (No at step S134), then the needle position polarity detection processing is executed (step S135). The needle position polarity detection processing will be described in detail later. If the step S135 is finished, then the process goes to the step S131.

Figure 23:
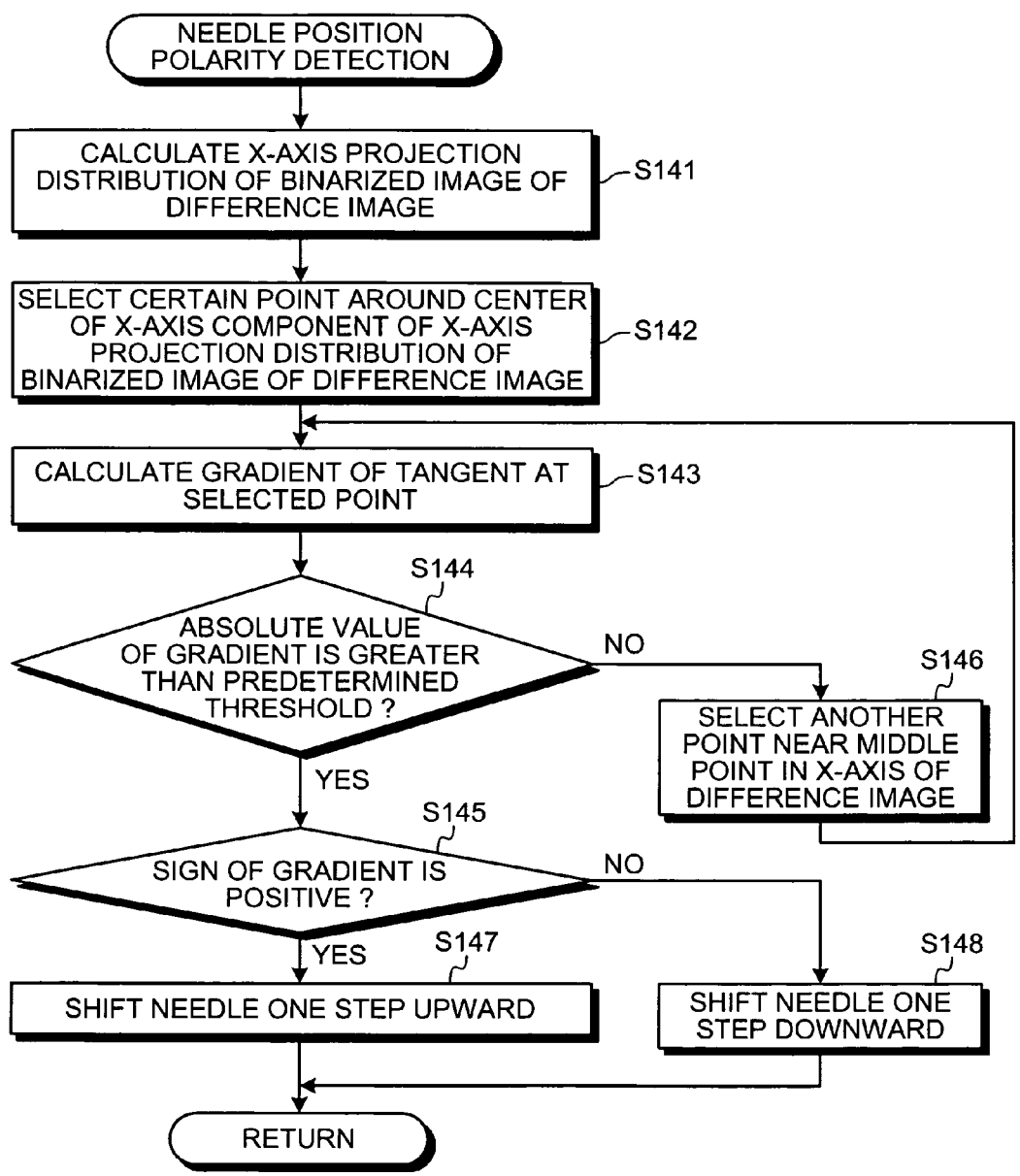
FIG. 23 is a flowchart of the needle position polarity detection processing procedure.

The needle position polarity detection processing will now be described. FIG. 23 is a flowchart of a detailed procedure of the needle position polarity detection processing shown in the step S135 of FIG. 22. As shown in FIG. 23, calculation is made of an X-axis projection distribution of the binarized image of the difference image (step S141). Then, one point is selected around the middle point of X-axis component on the X-axis projection distribution of the binarized image of the difference image (step S142) and calculation is made of a gradient of the tangent to the X-axis projection distribution curve at this selected point (step S143).

Judgment is then made as to whether an absolute value of the gradient calculated at step S143 is greater than the predetermined value (step S144). If it is judged that the absolute value is greater than the predetermined value (Yes at step S144), then judgement is made as to whether the sign of the gradient is positive (step S145). If it is not judged that the absolute value is greater than the predetermined value (No at step S144), then the process goes to step S146. If the step S146 is finished, then the process goes to the step S143.

At step S145, if it is judged that the sign of the gradient is positive (Yes at step S145), then the needle of the needle control stage 123 is shifted upward by one step (one shift unit) (step S157). On the other hand, if it is not judged that the sign of the gradient is positive (No at step S145), then the needle of the needle control stage 123 is shifted downward by one step (step S148). If the step S147 or step S148 is finished, then the process goes to the step S131 of the needle detection processing (FIG. 22).

Figure 24:
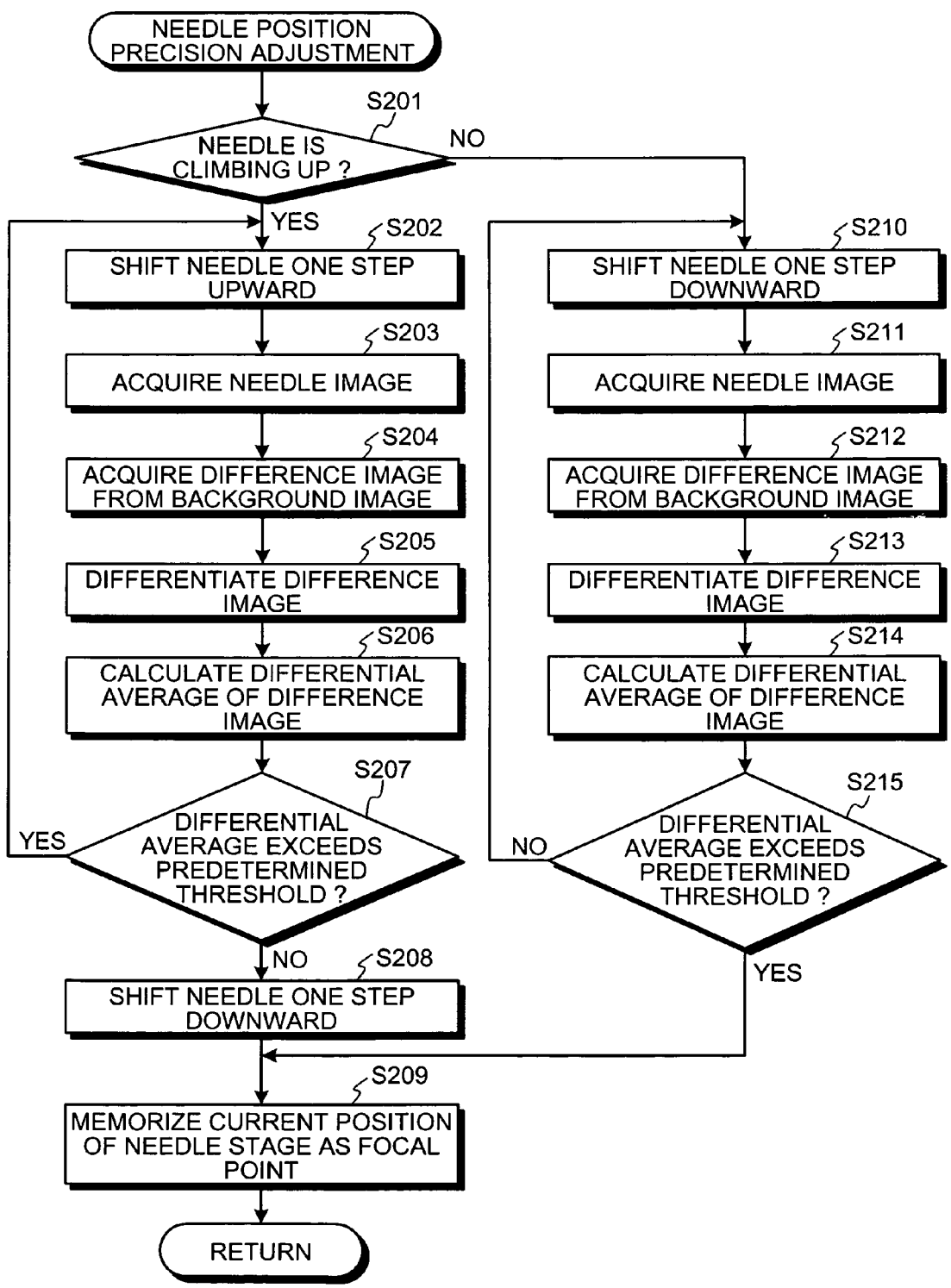
FIG. 24 is a flowchart of the needle position precision adjustment processing procedure.

The needle position precision adjustment processing will then be described. FIG. 24 is a flowchart of a detailed procedure of the needle position precision adjustment processing shown in the step S112 of FIG. 21. As shown in FIG. 24, judgment is made as to whether the needle is climbing up (step S201). If it is judged that the needle is climbing up (Yes at step S201), then the process goes to the step S202. If it is not judged that the needle is climbing up (No at step S201), then the process goes to the step S210.

At step S202, the needle is shifted upward by one step (one shift unit). Then, a needle image is acquired (step S203), a difference image is acquired of the background image and the needle image (step S204), the difference image is differentiated (step S205), and the differential average of the difference image is calculated (step S206).

Judgment is made as to whether the differential average exceeds the predetermined threshold (step S207). If it is judged that the differential average exceeds the predetermined threshold (Yes at step S207), then the process goes to the step S202, and if it is not judged that the differential average exceeds the predetermined threshold (No at step S207), then process goes to the step S208. At step S208, the needle is shifted downward by one step, and the current position of the needle stage is memorized as a focal point (step S209).

On the other hand, at step S210, the needle is shifted downward by one step (one shift unit). Then, a needle image is acquired (step S211), a difference-image is acquired of the background image and the needle image (step S212), the difference image is differentiated (step S213), and a differential average of the difference image is calculated (step S214).

Judgment is made as to whether the differential average exceeds the predetermined threshold (step S215). If it is judged that the differential average exceeds the predetermined-threshold (Yes at step S215), then the process goes to the step S209, and if it is not judged that the differential average exceeds the predetermined threshold (No at step S215), then process goes to the step S210.

By repeatedly executing the steps S202 to S207 or steps S210 to S215, the leading edge of the needle is shifted in a specific direction until the leading edge is judged to be in contact with the focal plane of the lens, and the work of the needle search can automatically be performed until the leading edge of the needle reaches the focal plane, and a reduced workload can be achieved.

While the embodiments of the present invention have been described above, the present invention is not limited thereto or thereby. Within the scope of the technological idea described in the scope of the note, the present invention may be embodied by further varied, different embodiments. The effects of the present invention are not limited to those described in the embodiments.

Specifically, the configuration and function blocks of the microinjection apparatus 100 and the controlling unit 150 thereof illustrated in the above-identified embodiments are illustrated only as an example, and to realize the microinjection apparatus and the microinjection method described in the scope of claims, the configuration and function blocks of the microinjection apparatus 100 and the controlling unit 150 thereof can be changed without departing from the scope of the claims.

The embodiments achieve an effect of being able to determine an operation start position of a needle with a low workload, with accuracy and speedily by moving a vertical position of the needle according to a shape of a leading edge of the needle as judged.

The embodiments also achieve an effect of being able to shift the needle to a focal plane of a lens with a low workload, accurately, and speedily by judging, when a differential aggregate based on an image of the leading edge of the needle taken at a position shifted to a given direction exceeds a first threshold, whether or not the leading edge of the needle is in contact with the focal plane of the lens, depending on a magnitude relation of a differential average of the image and a second threshold.

The embodiments further achieve an effect of being able to seek the position of the needle with a low workload, accurately and speedily by beginning the taking of an image including the leading edge of the needle, using the vertical position of the needle determined by use of an adherent cell.

Although the invention has been described with respect to a specific embodiment for a complete and clear disclosure, the appended claims are not to be thus limited but are to be construed as embodying all modifications and alternative constructions that may occur to one skilled in the art that fairly fall within the basic teaching herein set forth.

What is claimed is:

1. A microinjection apparatus that injects an object into an adherent cell with a needle, the needle being variable in its position in a first direction, the microinjection apparatus comprising:
   an image acquiring unit that acquires an image of a leading edge of the needle;
   a needle detecting unit that detects the leading edge of the needle in the image;
   a differential aggregate calculating unit that calculates a differential aggregate from the image of the leading edge of the needle detected by the needle detecting unit;
   a shape judging unit that determines a shape of the leading edge of the needle in the image when the differential aggregate calculated by the differential aggregate calculating unit is lower than a first threshold; and
   a needle shifting unit that shifts the needle in the first direction according to the shape of the leading edge judged by the shape judging unit.

2. The microinjection apparatus according to claim 1, wherein, after the needle shifting unit shifts the needle, the shape judging unit determines whether a differential aggregate calculated at shifted position is lower than the first threshold, the microinjection apparatus further comprising:
   a focus judging unit that, when the shape judging unit determines that the differential aggregate at the shifted position is lower than the first threshold, determines whether the leading edge of the needle is in a focal plane of the image acquiring unit based on comparison of the differential aggregate at the shifted position and a second threshold.

3. The microinjection apparatus according to claim 2, further comprising a storing unit that stores therein a position of the needle at which the focus judging unit judges that the leading edge of the needle is in the focal plane, distinguishing a petri dish having the base surface from another.

4. The microinjection apparatus according to claim 2, wherein the needle shifting unit further shifts the needle in the first direction when the focus judging unit judges that the leading edge of the needle is not in the focal plane.

5. The microinjection apparatus according to claim 1, further comprising:
   a first focal position detecting unit that detects a first focal position of the image acquiring unit at which a differential aggregate distribution according to focal positions of a first focal point interval comes to the maximum as calculated based on a difference image of a reference image that is an image of the cell acquired by the image acquiring unit at a standard focal position of the image acquiring unit and of the images of the cell acquired by the image acquiring unit at focal positions of the first focal point interval of the image acquiring unit, at an observation position of the cell at the base surface;
   a second focal position detecting unit that detects a second focal position of the image acquiring unit at which a differential aggregate distribution according to focal positions of a second focal point interval comes to the minimum as calculated based on a difference image of the reference image and the images of the cell acquired by the image acquiring unit at focal positions of the second focal point interval narrower than the first focal point interval within a predetermined range including the first focal position detected by the first focal position detecting unit at the observation position; and
   a needle position determining unit that determines a position of the needle in the first direction based on the second focal position, wherein
   the image acquiring unit starts to acquire an image including the leading edge of the needle, using the needle position determined by the needle position determining unit as a work start position.

6. The microinjection apparatus according to claim 5, wherein the needle position determining unit determines a position of the needle in first direction by adding a result of multiplying a variable of thickness of a bottom part by a refractive index when a variable of a position in first direction of the petri dish from a first standard value is small as compared with a variable of thickness of the bottom part of the petri dish from a second standard value.

7. The microinjection apparatus according to claim 1, wherein the needle keeps a given acute angle with a horizontal plane on which the base surface is arranged and is variable in its position in one specific direction on the horizontal plane and wherein the image acquiring unit starts to acquire an image including the leading edge of the needle, using the needle position to which the leading edge of the needle is offset by a predetermined volume in a direction forming a supplementary angle to the given acute angle on the horizontal plane as a work start position.

8. A method of microinjection of injecting an object into an adherent cell with a needle, the needle being variable in its position in a first direction, the method comprising one or more processors implementing the following:

acquiring a image of a leading edge of the needle with an image acquiring unit;

detecting the leading edge of the needle in the image;

calculating a differential aggregate from the image of the leading edge of the needle detected by the detecting;

determining a shape of the leading edge of the needle in the image when the differential aggregate calculated by the calculating is lower than a first threshold; and shifting the needle in the first direction according to the shape of the leading edge judged by the determining.

9. The method according to claim 8, wherein, after the needle is shifted at the shifting, it is determined at the determining whether a differential aggregate calculated at shifted position is lower than the first threshold, the method further comprising:

focus determining, when it is determined at the determining that the differential aggregate at the shifted position is lower than the first threshold, whether the leading edge of the needle is in a focal plane of the image acquiring unit based on comparison of the differential aggregate at the shifted position and a second threshold.

10. The method according to claim 9, wherein the shifting includes further shifting the needle in the first direction when it is determined at the focus determining that the leading edge of the needle is not in the focal plane.

11. The method according to claim 8, further comprising:

first detecting including detecting a first focal position of the image acquiring unit at which a differential aggregate distribution according to focal positions of a first focal point interval comes to the maximum as calculated based on a difference image of a reference image that is an image of the cell acquired by the image acquiring unit at a standard focal position of the image acquiring unit and of the images of the cell acquired by the image acquiring unit at focal positions of the first focal point interval of the image acquiring unit, at an observation position of the cell at the base surface;

second detecting of detecting a second focal position of the image acquiring unit at which a differential aggregate distribution according to focal positions of a second focal point interval comes to the minimum as calculated based on a difference image of the reference image and the images of the cell acquired by the image acquiring unit at focal positions of the second focal point interval narrower than the first focal point interval within a predetermined range including the first focal position detected at the first detecting at the observation position; and position determining of determining a position of the needle in the first direction based on the second focal position, wherein the image acquiring unit starts to acquire an image including the leading edge of the needle, using the needle position determined by the needle position determining unit as a work start position.

12. The microinjection apparatus according to claim 1, wherein, the shape judging unit judges the needle position is above or below a focal plane based on a change of a image width of the leading edge of the needle in the image; and the needle shifting unit shifts the needle to approach the focal plane based on the needle position judged by the shape judging unit.

13. The method according to claim 8, wherein, the determining includes judging the needle position is above or below a focal plane based on a change of a image width of the leading edge of the needle in the image; and the shifting includes shifting the needle to approach the focal plane based on the needle position judged by the determining.

* * * * *